US008741612B2

(12) United States Patent
Campbell et al.

(10) Patent No.: US 8,741,612 B2
(45) Date of Patent: Jun. 3, 2014

(54) MICROORGANISMS AND PROCESSES FOR THE PRODUCTION OF ISOPRENE

(71) Applicant: Glycos Biotechnologies, Inc., Houston, TX (US)

(72) Inventors: Paul Campbell, Houston, TX (US);
Sebastian Bredow, Houston, TX (US);
Huaijin Zhou, Houston, TX (US);
Stephanie Doneske, Katy, TX (US);
Daniel J. Monticello, The Woodlands, TX (US)

(73) Assignee: Glycos Biotechnologies, Inc., Houston, TX (US)

( * ) Notice: Subject to any disclaimer, the term of this patent is extended or adjusted under 35 U.S.C. 154(b) by 0 days.

(21) Appl. No.: 13/894,732

(22) Filed: May 15, 2013

(65) Prior Publication Data
US 2013/0309741 A1 Nov. 21, 2013

Related U.S. Application Data

(60) Provisional application No. 61/776,485, filed on Mar. 11, 2013, provisional application No. 61/688,514, filed on May 16, 2012.

(51) Int. Cl.
*C12P 5/02* (2006.01)
*C12N 1/20* (2006.01)
*C12N 1/00* (2006.01)
*C07C 13/00* (2006.01)
*C07C 9/00* (2006.01)
*C07C 7/00* (2006.01)

(52) U.S. Cl.
USPC .............. 435/167; 435/252.3; 435/254.11; 585/18; 585/16; 585/800

(58) Field of Classification Search
USPC .............. 435/167, 252.3, 254.11; 585/18, 16, 585/800
See application file for complete search history.

(56) References Cited

U.S. PATENT DOCUMENTS

| | | | |
|---|---|---|---|
| 5,849,970 | A | 12/1998 | Fall et al. |
| 7,659,097 | B2 * | 2/2010 | Renninger et al. ............ 435/157 |
| 8,420,360 | B2 | 4/2013 | Calabria et al. |
| 2007/0141574 | A1 | 6/2007 | Keasling et al. |
| 2009/0137014 | A1 | 5/2009 | Tsuruta et al. |
| 2010/0048964 | A1 | 2/2010 | Calabria et al. |
| 2010/0113846 | A1 | 5/2010 | McAuliffe et al. |
| 2010/0144893 | A1 | 6/2010 | Aharoni et al. |
| 2010/0331800 | A1 | 12/2010 | McPhee |
| 2012/0156745 | A1 | 6/2012 | Gray et al. |

FOREIGN PATENT DOCUMENTS

| | | |
|---|---|---|
| WO | 2009006429 A1 | 1/2009 |
| WO | 2011076689 A1 | 6/2011 |
| WO | 2011076691 A1 | 6/2011 |

OTHER PUBLICATIONS

Brodkorb et al., Linalool dehydratase-isomerase, a bifunctional enzyme in the anaerobic degradation of monoterpenes. J. Biol. Chem., vol. 285: 30436-30442.*
Gray et al., Biochemical charcterization and homology modeling of methylbutenol synthase and implications for understanding hemiterpene synthase in plants. J. Biol. Chem., 2011, vol. 286: 20582-20590.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Aharoni et al., Metabolic engineering of terpenoid biosynthesis in plants. Phytochem Rev., 2006, vol. 5: 49-58.*
Lucker et al., Expression of Clarkia S-linalool synthase in transgenic petunia plants results in the accumulation of S-linalyl-b-d-glucopyranoside. The Plant J., 2001, vol. 27 (4): 315-324.*
Co-pending U.S. Appl. No. 13/894,744.
Withers et al., "Identification of Isopentenol Biosynthetic Genes from *Bacillus subtilis* by a Screening Method Based on Isoprenoid Precursor Toxicity" Applied and Environmental Microbiology, 73 (19):6277-6283, 2007.
Turbek, C.S. et al., "Inducton and Purification of Klevitone Hydratase from *Fusarium solani* F. SP. Phaseoli," Phytochemistry, 29(9):2841-2846, 1990.
Li, D., et al., "The *Fusarium solani* Gene Encoding Kievitone Hydratase, a Secreted Enzyme that Catalyzes Detoxification of a Bean Phytoalexin," Molecular Plant-Microbe Interactions, 8(3):388-397, 1995.
Kisic, A., et al., "Oleate Hydratase: Studies of Substrate Specificity," LIPIDS, 6(8):4541-545, 1971.

(Continued)

*Primary Examiner* — Ganapathirama Raghu
(74) *Attorney, Agent, or Firm* — Darlene A. Vanstone, Esq.; Carolyn S. Elmore, Esq.; Elmore Patent Law Group, P.C.

(57) ABSTRACT

The present invention provides a novel biosynthetic pathway for the production of isoprene from 3-methyl-2-buten-1-ol or 2-methyl-3-buten-2-ol. Further embodiments provide non-naturally occurring microorganism that have been modified to produce isoprene from 3-methyl-2-buten-1-ol or 2-methyl-3-buten-2-ol and methods of producing isoprene using said microorganism.

20 Claims, 22 Drawing Sheets

(56) References Cited

OTHER PUBLICATIONS

Midelfort, K.S., "Redesigning and characerizng the substrate specificity and activity of *Vibtio fluvialis* aminotransferase for the synthesis of imagablin," Protein Engineering, Design & Selection, pp. 1-9, 2012.

Muller, R.H., et al., "Degradation of fuel oxygenates and their main intermediates by Aquincola tertiaricarbonis L108," Microbiology, 154:1414-1421, 2008.

Schafer, F., et al., "Synthesis of Short-Chain Diols and Unsaturated Alcohols from Secondary Alcohol Substrates by the Rieske Nonheme Mononuclear Iron Oxygenase MdpJ," Applied and Environmental Microbiology, 78 (17):6280-6284, 2012.

Schafer, F., et al., "Formation of Alkenes via Degradation of tert-Alkyl Ethers and Alcohols by Aquincola tertiaricarboni L108 and Methylibium spp.," Applied and Environmental Microbiology, 77(17):5981-5987, 2011.

Sivy, et al., "Evidence of Isoprenoid Precursor Toxicity in *Bacillus subtilis*," Biosci. Biotechnol. Biochem., 75 (12):2376-2383, 2011.

Kisic, A., et al., "Oleate Hydratase: Studies of Substrate Specificity," Lipids 6(8); pp. 541-545 (1971).

Van Leeuwen, B., et al, "Fermentative Production of Isobutene," Appl Microbiol Biotechnol 93:1377-1387 (2012).

Hiseni, A., et al., "Biochemical Characterization of the Carotenoid 1,2-hydratases (CrtC) from *Rubrivivax gelatinosus* and *Thiocapsa roseopersicina*", Appl Microbiol Biotechnol 91: 1029-1036 (2011).

Gupta, D., et al., "Engineering an Isoprenoid Pathway in *Escherichia coli* for Production of 2-Methyl-3-buten-2-ol: A Potential Biofuel," Mol Biotechnol, Nov. 2013.

Withers, S., et al, "Identification of Isopentenal Biosynthetic Genes from *Bacillus subtilis* by a Screening Method Based on Isoprenoid Precursor Toxicity," Applied and Environmental Microbiology, pp. 6277-6283 (Oct. 2007).

Baba, T., et al., "Construction of *Escherichia coli* K-12 in-frame, single-gene knockout mutants: the Keio collection," Molecular Systems Biology pp. 1-11 (2006).

\* cited by examiner

```
AGGAGGTAAAACATATGCACCACCATCATCACCACATGCGCTTTACGTTGAAAACCACCGCCAT
CGTGTCCGCTGCGGCGTTGCTGGCAGGTTTCGGTCCGCCACCGCGTGCGGCGGAGCTGCCGCCA
GGCCGTCTGGCGACCACCGAAGATTACTTCGCGCAACAAGCGAAACAGGCGGTGACGCCGGATG
TGATGGCACAACTGGCCTACATGAACTACATTGACTTCATCAGCCCGTTCTACAGCCGTGGTTG
CAGCTTTGAAGCGTGGGAGTTGAAGCATACGCCGCAACGCGTCATTAAGTATAGCATTGCGTTC
TATGCATACGGTCTGGCGTCGGTCGCACTGATTGACCCGAAGCTGCGTGCCCTGGCAGGTCACG
ATCTGGATATCGCGGTGTCTAAAATGAAGTGCAAGCGTGTTTGGGGTGACTGGGAAGAGGATGG
TTTTGGCACCGACCCGATCGAGAAAGAGAACATCATGTACAAAGGTCATCTGAACCTGATGTAT
GGCCTGTATCAGCTGGTGACGGGTAGCCGTCGCTACGAGGCAGAGCACGCGCACCTGACCCGTA
TCATCCATGACGAGATTGCCGCTAATCCGTTCGCCGGCATCGTATGTGAACCGGACAATTACTT
TGTCCAGTGTAACAGCGTCGCGTACTTGAGCCTGTGGGTTTATGACCGTCTGCACGGCACTGAT
TATCGCGCAGCCACCCGTGCTTGGTTGGATTTCATTCAGAAGGACCTGATCGACCCGGAGCGCG
GTGCATTCTACCTGTCTTACCACCCGGAAAGCGGTGCTGTTAAGCCGTGGATTAGCGCGTATAC
CACTGCATGGACGCTGGCCATGGTTCACGGCATGGATCCGGCGTTTAGCGAGCGCTACTATCCG
CGCTTCAAACAGACCTTCGTTGAAGTGTACGACGAGGGCCGTAAAGCCCGGGTTCGTGAAACCG
CCGGTACCGACGACGCCGACGGTGGCGTGGGTCTGGCGAGCGCGTTTACGCTGTTGTTGGCACG
TGAGATGGGCGATCAGCAACTGTTTGATCAGCTGCTGAATCATCTGGAACCGCCTGCCAAACCG
AGCATTGTCAGCGCGTCCCTGCGTTATGAACACCCTGGCTCCCTGCTGTTTGATGAGCTGCTGT
TCCTGGCTAAAGTTCATGCAGGTTTTGGTGCGCTGCTGCGTATGCCGCCACCGGCAGCGAAGCT
GGCGGGCAAGTAACTCGAG (SEQ ID NO: 1)
```

Fig. 3

```
AGGAGGTAAAACATATGCATCATCACCACCACCACATGGAAAAGATCGAGGTAAGCATTAACAG
CAAACATACGATTAAACCGAGCACGAGCTCCACCCCGTTGCAGCCGTATAAGCTGACCCTGCTG
GACCAACTGACCCCACCGGCATACGTCCCAATCGTCTTTTTCTATCCGATTACGGATCACGACT
TCAATCTGCCGCAGACGCTGGCAGACCTGCGTCAAGCCCTGTCCGAAACCCTGACTCTGTATTA
CCCGCTGAGCGGTCGTGTGAAGAATAACTTGTACATTGACGACTTCGAAGAGGGCGTTCCGTAC
CTGGAAGCGCGTGTCAATTGTGATATGACGGACTTCCTGCGCCTGCGTAAGATTGAGTGTTTGA
ACGAGTTCGTGCCGATTAAGCCGTTTAGCATGGAAGCCATTAGCGACGAGCGTTACCCGTTGCT
GGGTGTTCAAGTCAACGTGTTCGATAGCGGTATCGCGATCGGTGTTTCGGTTTCTCATAAACTG
ATCGACGGCGGCACCGCGGACTGCTTCCTGAAATCCTGGGGTGCGGTTTTCCGCGGTTGCCGCG
AGAATATCATCCACCCGAGCCTGAGCGAGGCGGCACTGCTGTTCCCACCGCGCGATGATTTGCC
GGAGAAATATGTTGATCAGATGGAAGCCCTGTGGTTCGCGGGTAAAAAGGTTGCGACCCGTCGC
TTTGTCTTTGGTGTTAAGGCGATCAGCAGCATCCAGGACGAGGCAAAGTCTGAATCGGTGCCTA
AGCCGTCCCGTGTGCACGCGGTCACCGGCTTTCTGTGGAAGCACCTGATTGCGGCAAGCCGTGC
TCTGACCTCTGGCACCACCTCGACGCGCCTGAGCATTGCGGCACAGGCCGTTAATCTGCGTACC
CGCATGAACATGGAAACTGTGCTGGACAATGCGACCGGCAACCTGTTTTGGTGGGCGCAGGCTA
TTCTGGAGTTGAGCCACACCACCCCGGAGATCAGCGATCTGAAGCTGTGCGATCTGGTGAACTT
GTTGAATGGCAGCGTTAAACAATGCAATGGTGATTACTTCGAAACGTTTAAAGGTAAAGAGGGC
TATGGCCGTATGTGTGAATATCTGGATTTTCAGCGTACGATGAGCAGCATGGAGCCGGCACCGG
ATATCTACCTGTTTAGCAGCTGGACGAACTTCTTTAACCCGCTGGACTTTGGTTGGGGTCGTAC
CAGCTGGATCGGTGTCGCAGGTAAGATCGAGAGCGCCAGCTGCAAATTCATTATTCTGGTGCCT
ACCCAATGTGGCTCTGGTATCGAGGCTTGGGTGAACCTGGAAGAAGAGAAAATGGCCATGCTGG
AACAAGACCCGCATTTCCTGGCGCTGGCTAGCCCGAAAACCTTGATTTAACTCGAG
(SEQ ID NO: 2)
```

Fig. 4

3-methyl-2-buten-1-ol in LB Medium 3-methyl-2-buten-1-ol + BL21 (pJ404-LDI)

2-methyl-3-buten-2-ol in LB Medium 2-methyl-3-buten-2-ol + BL21 (pJ404-LDI)

```
ATTAAAGAGGAGAAAATATAATGACGGCAGTATGCCTGGTCCGCCACGGCGAAACCGATTGGAACCTGCAACAGAAA
TGCCAGGGTAAAACCGATATCCCGCTGAATGCGACGGGCGAACGTCAGGCCCGTGAAACGGGTGAATACGTCAAAGA
CTTTAGCTGGGACATCATTGTTACCAGCCCGCTGAAGCGCGCCAAGCGTACGGCTGAGATCATCAATGAATACCTGC
ATCTGCCGATCGTTGAAATGGACGACTTTAAAGAGCGCGATTATGGCGATGCTGAGGGTATGCCGTTGGAGGAGCGC
ACCAAGCGTTATCCGGACAACATTTATCCGAACATGGAGACTCTGGAAGAGCTGACGGACCGTTTGATGGGCGGTCT
GGCAAAAGTCAATCAGGCATACCCGAACAAAAAGGTGCTGATCGTTGCACATGGTGCGGCAATTCACGCGCTGCTGA
CGGAGATTTCTGGTGGTGACCCGGAGCTGCAAAGCACCCGTCTGGTCAATGCGTGTTTGTCGAATATTGAATTTGCG
GAAGAAAAGTGGCGTATCAAAGACTACAACATTAACTCCCATCTGAGCGGTTTCATCAAATAA(SEQ ID NO: 3)
```

Fig. 11

```
GGTACCTTAATTAATATAAGGAGGTAAAACATATGAACGTTGAAACCAAACACACGCGCACGATGGGTGACATTTTT
GTACAACATAGCCAGAAACTGGAACTGCTGAAAACCGTCCTGCGTAACGTCGCTGAGCTGGACGCACTGGAAGGCTT
GAACATGATTGACGCGGTGCAGCGTTTGGGTATCGACTACAATTTTCAGCGTGAGATTGACGAGATTCTGCACAAGC
AGATGAGCATCGTCAGCGCGCGTGACGACTTGCACGAGGTTGCGCTGCGCTTCCGTCTGCTGCGCCAGCATGGCTAT
TTCGTCCCAGAGGATGTTTTCAACAATTTCAAGGACTCGAAAGGTACGTTCAAACAGGTGCTGGGTGAGGACATCAA
GGGCCTGATGAGCCTGTACGAGGCGAGCCAACTGGGCACCGAGGGCGAGGACATTCTGGTTGAAGCGGAGAAGTTCA
GCGGCCACTTGCTGAAAACGAGCCTGAGCCACCTGGATCATCATCGTGTGCGTATTGTGGCGAATACCTTGCGCAAT
CCGCACCACAAAAGCCTGGCGCCTTTCATGGCACGTAACTTTTTCGTTACGAGCCAAGCTACTAATAGCTGGCTGAA
TCTGTTGAAAGAGGTCGCCAAGACGGACTTCAATATGGTGCGCTCTCTGCACCAAAATGAGATTGTTCAGATGTCCA
AATGGTGGAAAGAGCTGGGCCTGGCCAAAGAGCTGAAGTTCGCCCGTGACCAGCCGCTGAAGTGGTACATTTGGAGC
ATGGCGTGCCTGACCGATCCGAAACTGAGCGAAGAGCGTGTTGAGCTGACGAAGCCAATCAGCTTTGTTTACTTGAT
TGACGATATCTTTGACGTTTACGGCACGCTGGACGACCTGATCCTGTTTACCGAGGCCGTTAATCGTTGGGAGATCA
CGGCGATCGACCACTTGCCTGACTATATGAAGATTTGTTTTAAGGCATTGTACGATATGACCAATGAGTTTAGCAGC
AAGGTCTATCTGAAACATGGCTGGAACCCGCTGCAAAGCCTGAAAATCAGCTGGGCGAGCTTGTGTAACGCATTCCT
GGTCGAGGCCAAGTGGTTTGCGAGCGGTAAGCTGCCGAAAAGCGAAGAGTATTTGAAGAATGGTATTGTGAGCAGCG
GTGTTAATGTGGTGCTGGTGCACATGTTTTTCCTGCTGGGTCAAAACATCACCCGCAAATCTGTCGAGCTGCTGAAC
GAAACTCCGGCGATCATTAGCTCTAGCGCTGCGATCCTGCGCCTGTGGGATGATTTGGGTAGCGCGAAGGACGAGAA
TCAAGACGGTAACGATGGTAGCTATGTTCGTTGCTACCTGGAAGAACACGAAGGTTGCAGCATCGAAGAAGCGCGCG
AGAAAACCATCAACATGATTAGCGATGAGTGGAAGAAGTTGAATCGCGAGTTGCTGAGCCCGAACCCGTTCCCAGCA
AGCTTCACCCTGGCGAGCCTGAACCTGGCACGTATGATCCCGCTGATGTACTCCTACGACGGTAATCAGTGCCTGCC
TTCCCTGAAAGAGTATATGAAGCTGATGCTGTACGAAACCGTCAGCATGTGATGAGGAATAAAATTATGCTGCGTAG
CCTGCTGCGTGGCCTGACCCACTTTCCGCGTGTGAACTCCGCTCAACAACCGTCGTGCGCCCATGCCCGCCTGCAAT
TTCGTCCGCGCAGCATGCAGCTGCTGGCCGAAGATCGTACCGACCACATGCGTGGTGCTAGTACGTGGGCGGGCGGT
CAATCCCAAGATGAACTGATGCTGAAAGACGAATGCATTCTGGTCGATGCGGATGACAACATCACCGGTCATGTGAG
CAAACTGGAATGTCATAAGTTTCTGCCGCACCAGCCGGCGGGTCTGCTGCACCGTGCATTCTCTGTTTTTCTGTTCG
ATGACCAGGGTCGCCTGCTGCTGCAGCAACGTGCCCGCAGCAAGATTACCTTTCCGTCTGTTTGGACCAATACGTGC
TGTTCACATCCGCTGCACGGCCAGACCCCGGATGAAGTGGATCAGCTGTCGCAAGTGGCTGATGGCACGGTTCCGGG
TGCAAAAGCGGCGGCAATTCGTAAGCTGGAACATGAACTGGGTATCCCGGCACACCAGCTGCCGGCAAGTGCATTTC
GTTTCCTGACCCGCCTGCATTATTGTGCTGCCGATGTTCAGCCGGCGGCAACCCAATCAGCCCTGTGGGGCGAACAC
GAAATGGATTACATTCTGTTCATCCGTGCTAACGTGACCCTGGCGCCGAATCCGGATGAAGTGGACGAAGTTCGTTA
TGTCACGCAGGAAGAACTGCGCCAGATGATGCAACCGGATAACGGTCTGCAATGGTCCCCGTGGTTTCGCATTATCG
CTGCGCGTTTCCTGGAACGTTGGTGGGCCGATCTGGACGCAGCACTGAACACCGATAAACACGAAGACTGGGGCACC
GTCCATCACATCAACGAAGCATAACCATGG (SEQ ID NO: 4)
```

Fig. 12

```
GGATCCTCCCTATCAGTGATAGAGATTGACATCCCTATCAGTGATAGAGATACTGAGCACATCAGCAGGACGCACTG
ACCGGTACCTTTGAATTCCCCACGCGTAGATCTCTAGATGTACACCATGGGCTAGAGGCATCAAATAAAACGAAAGG
CTCAGTCGAAAGACTGGGCCTTTCGTTTTATCTGTTGTTTGTCGGTGAACGCTCTCCTGAGTAGGACAAATCCGCCG
CCCTAGACCTAGGCGTTCGGCTGCGGCGAGCGGTATCAGCTCACTCAAAGGCGGTAATACGGTTATCCACAGAATCA
GGGGATAACGCAGGAAAGAACATGTGAGCAAAAGGCCAGCAAAAGGCCAGGAACCGTAAAAACGCGCTAGCGGAGTG
TATACTGGCTTACTATGTTGGCACTGATGAGGGTGTCAGTGAAGTGCTTCATGTGGCAGGAGAAAAAAGGCTGCACC
GGTGCGTCAGCAGAATATGTGATACAGGATATATTCCGCTTCCTCGCTCACTGACTCGCTACGCTCGGTCGTTCGAC
TGCGGCGAGCGGAAATGGCTTACGAACGGGGCGGAGATTTCCTGGAAGATGCCAGGAAGATACTTAACAGGGAAGTG
AGAGGGCCGCGGCAAAGCCGTTTTTCCATAGGCTCCGCCCCCCTGACAAGCATCACGAAATCTGACGCTCAAATCAG
TGGTGGCGAAACCCGACAGGACTATAAAGATACCAGGCGTTTCCCCCTGGCGGCTCCCTCGTGCGCTCTCCTGTTCC
TGCCTTTCGGTTTACCGGTGTCATTCCGCTGTTATGGCCGCGTTTGTCTCATTCCACGCCTGACACTCAGTTCCGGG
TAGGCAGTTCGCTCCAAGCTGGACTGTATGCACGAACCCCCCGTTCAGTCCGACCGCTGCGCCTTATCCGGTAACTA
TCGTCTTGAGTCCAACCCGGAAAGACATGCAAAAGCACCACTGGCAGCAGCCACTGGTAATTGATTTAGAGGAGTTA
GTCTTGAAGTCATGCGCCGGTTAAGGCTAAACTGAAAGGACAAGTTTTGGTGACTGCGCTCCTCCAAGCCAGTTACC
TCGGTTCAAAGAGTTGGTAGCTCAGAGAACCTTCGAAAAACCGCCCTGCAAGGCGGTTTTTTCGTTTTCAGAGCAAG
AGATTACGCGCAGACCAAAACGATCTCAAGAAGATCATCTTATTAAGTGGCCTAACTACGGCTACACTAGAAGGACA
GTATTTGGTATCTGCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCTCAAGAAGATCCTT
TGATCTTTTCTACGGGGTCTGACGCTCAGTGGAACGAAAACTCACGTTAAGGGATTTTGGTCATGACTAGTGCTTGG
ATTCTCACCAATAAAAAACGCCCGGCGGCAACCGAGCGTTCTGAACAAATCCAGATGGAGTTCTGAGGTCATTACTG
GATCTATCAACAGGAGTCCAAGCGAGCTCGATATCAAATTACGCCCCGCCCTGCCACTCATCGCAGTACTGTTGTAA
TTCATTAAGCATTCTGCCGACATGGAAGCCATCACAGACGGCATGATGAACCTGAATCGCCAGCGGCATCAGCACCT
TGTCGCCTTGCGTATAATATTTGCCCATCGTGAAAACGGGGGCGAAGAAGTTGTCCATATTGGCCACGTTTAAATCA
AAACTGGTGAAACTCACCCAGGGATTGGCTGAGACGAAAAACATATTCTCAATAAACCCTTTAGGGAAATAGGCCAG
GTTTTCACCGTAACACGCCACATCTTGCGAATATATGTGTAGAAACTGCCGGAAATCGTCGTGGTATTCACTCCAGA
GCGATGAAAACGTTTCAGTTTGCTCATGGAAAACGGTGTAACAAGGGTGAACACTATCCCATATCACCAGCTCACCG
TCTTTCATTGCCATACGGAACTCCGGATGAGCATTCATCAGGCGGGCAAGAATGTGAATAAAGGCCGGATAAAACTT
GTGCTTATTTTCTTTACGGTCTTTAAAAAGGCCGTAATATCCAGCTGAACGGTCTGGTTATAGGTACATTGAGCAA
CTGACTGAAATGCCTCAAAATGTTCTTTACGATGCCATTGGGATATATCAACGGTGGTATATCCAGTGATTTTTTC
TCCATTTTAGCTTCCTTAGCTCCTGAAAATCTCGATAACTCAAAAAATACGCCCGGTAGTGATCTTATTTCATTATG
GTGAAAGTTGGAACCTCTTACGTGCCGATCAACGTCTCATTTTCGCCAGATATCGACGTCGTCATCAAACCTGTCGC
GCACTCTAGGCTACTCAGCTACTAGAAAGCTTAAGACCCACTTTCACATTTAAGTTGTTTTTCTAATCCGCAGATGA
TCAATTCAAGGCCGAATAAGAAGGCTGGCTCTGCACCTTGGTGATCAAATAATTCGATAGCTTGTCGTAATAATGGC
GGCATACTATCAGTAGTAGGTGTTTCCCTTTCTTCTTTAGCGACTTGATGCTCTTGATCTTCCAATACGCAACCTAA
AGTAAAATGCCCCACAGCGCTGAGTGCATATAATGCATTCTCTAGTGAAAAACCTTGTTGGCATAAAAAGGCTAATT
GATTTTCGAGAGTTTCATACTGTTTTTCTGTAGGCCGTGTACCTAAATGTACTTTTGCTCCATCGCGATGACTTAGT
AAAGCACATCTAAAACTTTTAGCCTTATTACGTAAAAAATCTTGCCAGCTTTCCCCTTCTAAAGGGCAAAAGTGAGT
ATGGTGCCTATCTAACATCTCAATGGCTAAGGCGTCGAGCAAAGCCCGCTTATTTTTACATGCCAATACAATGTAG
GCTGCTCTACACCTAGCTTCTGGGCGAGTTTACGGGTTGTTAAACCTTCGATTCCGACCTCATTAAGCAGCTCTAAT
GCGCTGTTAATCACTTTACTTTTATCTAATCTTAACATGTGAATACGGGGCGGGATTTCATGGATATGTTTCTTTCT
GCGAGAACCAGCCATATTTAAACTCTTCTCTCAAATTTATGAATCTATTATACAGAAAAATTTTCCTGAAAGCAAAT
AAATTTTTTATGATTTCCCTCGACAATTCGCGCTAACTTACATTAATTGCGTTGCGCTCACTGCCCGCTTT
(SEQ ID NO: 5)
```

Fig. 21

```
GGATCCTCCCTATCAGTGATAGAGATTGACATCCCTATCAGTGATAGAGATACTGAGCACATCAGCAGGACGCACTGAC
CGGTACCTTTGAATTCCCCACGCGTAGATCTCTAGATGTACACCATGGGCTAGAGGCATCAAATAAAACGAAAGGCTCA
GTCGAAAGACTGGGCCTTTCGTTTTATCTGTTGTTTGTCGGTGAACGCTCTCCTGAGTAGGACAAATCCGCCGCCCTAG
ACCTAGGGTACGGGTTTTGCTGCCCGCAAACGGGCTGTTCTGGTGTTGCTAGTTTGTTATCAGAATCGCAGATCCGGCT
TCAGGTTTGCCGGCTGAAAGCGCTATTTCTTCCAGAATTGCCATGATTTTTTCCCCACGGGAGGCGTCACTGGCTCCCG
TGTTGTCGGCAGCTTTGATTCGATAAGCAGCATCGCCTGTTTCAGGCTGTCTATGTGTGACTGTTGAGCTGTAACAAGT
TGTCTCAGGTGTTCAATTTCATGTTCTAGTTGCTTTGTTTTACTGGTTTCACCTGTTCTATTAGGTGTTACATGCTGTT
CATCTGTTACATTGTCGATCTGTTCATGGTGAACAGCTTTAAATGCACCAAAAACTCGTAAAAGCTCTGATGTATCTAT
CTTTTTTACACCGTTTTCATCTGTGCATATGGACAGTTTTCCCTTTGATATCTAACGGTGAACAGTTGTTCTACTTTTG
TTTGTTAGTCTTGATGCTTCACTGATAGATACAAGAGCCATAAGAACCTCAGATCCTTCCGTATTTAGCCAGTATGTTC
TCTAGTGTGGTTCGTTGTTTTGCGTGAGCCATGAGAACGAACCATTGAGATCATGCTTACTTTGCATGTCACTCAAAA
ATTTTGCCTCAAAACTGGTGAGCTGAATTTTTGCAGTTAAAGCATCGTGTAGTGTTTTCTTAGTCCGTTACGTAGGTA
GGAATCTGATGTAATGGTTGTTGGTATTTTGTCACCATTCATTTTTATCTGGTTGTTCTCAAGTTCGGTTACGAGATCC
ATTTGTCTATCTAGTTCAACTTGGAAAATCAACGTATCAGTCGGGCGGCCTCGCTTATCAACCACCAATTTCATATTGC
TGTAAGTGTTTAAATCTTTACTTATTGGTTTCAAAACCCATTGGTTAAGCCTTTTAAACTCATGGTAGTTATTTTCAAG
CATTAACATGAACTTAAATTCATCAAGGCTAATCTCTATATTTGCCTTGTGAGTTTTCTTTTGTGTTAGTTCTTTTAAT
AACCACTCATAAATCCTCATAGAGTATTTGTTTTCAAAAGACTTAACATGTTCCAGATTATATTTTATGAATTTTTTTA
ACTGGAAAAGATAAGGCAATATCTCTTCACTAAAAACTAATTCTAATTTTTCGCTTGAGAACTTGGCATAGTTTGTCCA
CTGGAAAATCTCAAAGCCTTTAACCAAAGGATTCCTGATTTCCACAGTTCTCGTCATCAGCTCTCTGGTTGCTTTAGCT
AATACACCATAAGCATTTTCCCTACTGATGTTCATCATCTGAGCGTATTGGTTATAAGTGAACGATACCGTCCGTTCTT
TCCTTGTAGGGTTTTCAATCGTGGGGTTGAGTAGTGCCACACAGCATAAAATTAGCTTGGTTTCATGCTCCGTTAAGTC
ATAGCGACTAATCGCTAGTTCATTTGCTTTGAAAACAACTAATTCAGACATACATCTCAATTGGTCTAGGTGATTTTAA
TCACTATACCAATTGAGATGGGCTAGTCAATGATAATTACTAGTCCTTTTCCCGGGAGATCTGGGTATCTGTAAATTCT
GCTAGACCTTTGCTGGAAAACTTGTAAATTCTGCTAGACCCTCGTAAATTCCGCTAAGACCTTTGTGTGTTTTTTTTGT
TTATATTCAAGTGGTTATAAATTTATAGAATAAAGAAAGAATAAAAAAAGATAAAAAGAATAGATCCCAGCCCTGTGTAT
AACTCACTACTTTAGTCAGTTCCGCAGTATTACAAAAGGATGTCGCAAACGCTGTTTGCTCCTCTACAAAACAGACCTT
AAAACCCTAAAGGCTTAAGTAGCACCCTCGCAAGCTCGGGCAAATCGCTGAATATTCCTTTTGTCTCCGACCATCAGGC
ACCTGAGTCGCTGTCTTTTTCGTGACATTCAGTTCGCTGCGCTCACGGCTCTGGCAGTGAATGGGGTAAATGGCACTA
CAGGCGCCTTTTATGGATTCATGCAAGGAAACTACCCATAATACAAGAAAAGCCCGTCACGGGCTTCTCAGGGCGTTTT
ATGGCGGGTCTGCTATGTGGTGCTATCTGACTTTTTGCTGTTCAGCAGTTCCTGCCCTCTGATTTTCCAGTCTGACCAC
TTCGGATTATCCCGTGACAGGTCATTCAGACTGGCTAATGCACCCAGTAAGGCAGCGGTATCATCAACAGGCTTACCCG
TCTTACTGTCCCTAGTGCTTGGATTCTCACCAATAAAAAACGCCCGGCGGCAACCGAGCGTTCTGAACAAATCCAGATG
GAGTTCTGAGGTCATTACTGGATCTATCAACAGGAGTCCAAGCGAGCTCGATATCAAATTACGCCCCGCCCTGCCACTC
ATCGCAGTACTGTTGTAATTCATTAAGCATTCTGCCGACATGGAAGCCATCACAGACGGCATGATGAACCTGAATCGCC
AGCGGCATCAGCACCTTGTCGCCTTGCGTATAATATTTGCCCATCGTGAAAACGGGGCGAAGAAGTTGTCCATATTGG
CCACGTTTAAATCAAAACTGGTGAAACTCACCCAGGGATTGGCTGAGACGAAAAACATATTCTCAATAAACCCTTTAGG
GAAATAGGCCAGGTTTTCACCGTAACACGCCACATCTTGCGAATATATGTGTAGAAACTGCCGGAAATCGTCGTGGTAT
TCACTCCAGAGCGATGAAAACGTTTCAGTTTGCTCATGGAAAACGGTGTAACAAGGGTGAACACTATCCCATATCACCA
GCTCACCGTCTTTCATTGCCATACGGAACTCCGGATGAGCATTCATCAGGCGGGCAAGAATGTGAATAAAGGCCGGATA
AAACTTGTGCTTATTTTTCTTTACGGTCTTTAAAAAGGCCGTAATATCCAGCTGAACGGTCTGGTTATAGGTACATTGA
GCAACTGACTGAAATGCCTCAAAATGTTCTTTACGATGCCATTGGGATATATCAACGGTGGTATATCCAGTGATTTTTT
TCTCCATTTTAGCTTCCTTAGCTCCTGAAAATCTCGATAACTCAAAAAATACGCCCGGTAGTGATCTTATTTCATTATG
GTGAAAGTTGGAACCTCTTACGTGCCGATCAACGTCTCATTTTCGCCAGATATCGACGTCGTCATCAAACCTGTCGCGC
ACTCTAGGCTACTCAGCTACTAGAAAAGCTTAAGACCCACTTTCACATTTAAGTTGTTTTTCTAATCCGCAGATGATCAA
TTCAAGGCCGAATAAGAAGGCTGGCTCTGCACCTTGGTGATCAAATAATTCGATAGCTTGTCGTAATAATGGCGGCATA
CTATCAGTAGTAGGTGTTTCCCTTTCTTCTTTAGCGACTTGATGCTCTTGATCTTCCAATACGCAACCTAAAGTAAAAT
GCCCCACAGCGCTGAGTGCATATAATGCATTCTCTAGTGAAAAACCTTGTTGGCATAAAAAGGCTAATTGATTTTCGAG
AGTTTCATACTGTTTTTCTGTAGGCCGTGTACCTAAATGTACTTTTGCTCCATCGCGATGACTTAGTAAAGCACATCTA
AAACTTTTAGCCTTATTACGTAAAAAATCTTGCCAGCTTTCCCCTTCTAAAGGGCAAAGTGAGTATGGTGCCTATCTA
ACATCTCAATGGCTAAGGCGTCGAGCAAAGCCCGCTTATTTTTACATGCCAATACAATGTAGGCTGCTCTACACCTAG
CTTCTGGGCGAGTTTACGGGTTGTTAAACCTTCGATTCCGACCTCATTAAGCAGCTCTAATGCGCTGTTAATCACTTTA
CTTTTATCTAATCTTAACATGTGAATACGGGCGGGATTTCATGGATATGTTTCTTTCTGCGAGAACCAGCCATATTTA
AACTCTTCTCTCAAATTTATGAATCTATTATACAGAAAATTTTCCTGAAAGCAAATAAATTTTTATGATTTCCCTCG
ACAATTCGCGCTAACTTACATTAATTGCGTTGCGCTCACTGCCCGCTTT (SEQ ID NO: 6)
```

Fig. 22

```
GGTACCATTAAAGAGGAGAAAATATAATGAAAACTGTAGTAATCATCGACGCCCTGCGCACGCCAATCGGCAAGTAT
AAGGGTTCTCTGAGCCAAGTTAGCGCAGTCGATCTGGGCACCCATGTCACGACCCAGTTGCTGAAGCGTCATTCCAC
CATCAGCGAGGAAATTGATCAGGTGATCTTCGGTAACGTCCTGCAAGCCGGCAATGGTCAGAACCCTGCGCGTCAGA
TTGCGATTAACTCTGGCTTGAGCCACGAGATCCCGGCTATGACGGTGAATGAGGTTTGTGGCAGCGGTATGAAGGCG
GTTATCTTGGCAAAACAGCTGATCCAGTTGGGTGAGGCCGAGGTACTGATTGCGGGTGGTATCGAAAACATGAGCCA
GGCGCCAAAATTGCAACGTTTTAACTATGAAACTGAAAGCTATGACGCGCCGTTTTCCAGCATGATGTACGACGGTC
TGACCGATGCGTTCAGCGGTCAGGCGATGGGCCTGACTGCGGAGAATGTGGCGGAGAAGTACCACGTCACTCGTGAA
GAACAAGACCAGTTTAGCGTGCATTCCCAGCTGAAAGCGGCGCAAGCACAAGCAGAGGGTATCTTCGCAGACGAAAT
CGCGCCGTTGGAGGTGAGCGGCACGCTGGTTGAGAAAGATGAGGGTATCCGCCCTAATTCTAGCGTGGAAAAGCTGG
GTACTCTGAAAACCGTTTTCAAAGAGGACGGTACGGTTACGGCCGGTAACGCGAGCACCATCAATGATGGTGCGAGC
GCCCTGATTATCGCAAGCCAGGAGTACGCAGAGGCTCACGGTCTGCCGTACCTGGCGATTATCCGTGACAGCGTTGA
AGTGGGTATCGATCCGGCATATATGGGTATCAGCCCGATTAAGGCAATTCAGAAATTGCTGGCCCGTAACCAGCTGA
CCACGGAGGAGATTGATCTGTACGAGATTAACGAGGCGTTTGCAGCAACTAGCATCGTTGTGCAGCGTGAGTTGGCC
CTGCCGGAGGAGAAAGTTAACATTTACGGTGGCGGTATCAGCTTGGGTCATGCAATCGGCGCCACGGGCGCTCGTCT
GCTGACCTCCCTGAGCTACCAACTGAATCAGAAGGAGAAGAAATACGGCGTTGCCAGCCTGTGCATTGGCGGTGGCC
TGGGTCTGGCCATGCTGTTGGAACGTCCGCAACAGAAGAAGAATTCACGTTTTTACCAAATGAGCCCGGAGGAGCGT
TTGGCCAGCCTGCTGAATGAGGGTCAGATTAGCGCGGATACCAAGAAAGAATTTGAAAACACCGCGCTGAGCAGCCA
GATTGCTAATCACATGATTGAGAACCAGATCAGCGAAACCGAAGTGCCGATGGGTGTTGGCCTGCACCTGACGGTTG
ATGAAACCGATTACCTGGTTCCGATGGCAACCGAAGAACCTAGCGTTATTGCAGCACTGAGCAACGGTGCAAAGATC
GCTCAGGGCTTCAAAACGGTCAATCAGCAGCGTCTGATGCGTGGCCAAATTGTCTTTTATGATGTGGCAGACCCGGA
GTCCTTGATCGACAAGCTGCAAGTACGTGAGGCGGAAGTTTTCCAACAGGCGGAGCTGAGCTATCCGAGCATCGTCA
AGCGCGGTGGTGGTCTGCGTGACCTGCAATACCGCACGTTTGATGAGAGCTTTGTTAGCGTGGACTTTCTGGTGGAC
GTGAAGGACGCGATGGGTGCCAATATCGTTAATGCAATGCTGGAGGGTGTGGCGGAACTGTTTCGCGAATGGTTCGC
AGAACAAAAGATTCTGTTCAGCATTTTGAGCAACTACGCCACCGAATCGGTAGTTACGATGAAAACCGCGATTCCAG
TGTCTCGTCTGAGCAAGGGTAGCAATGGTCGTGAAATCGCCGAGAAAATTGTGCTGGCCAGCCGCTACGCGAGCCTG
GACCCGTATCGCGCGGTTACCCACAATAAGGGTATCATGAATGGCATTGAAGCGGTCGTTCTGGCCACGGGCAATGA
CACCCGTGCGGTGAGCGCTTCCTGCCACGCATTTGCTGTTAAAGAGGGCCGTTACCAGGGCCTGACCTCGTGGACCC
TGGATGGTGAGCAACTGATCGGCGAGATCAGCGTTCCGTTGGCACTGGCCACCGTGGGTGGTGCGACCAAAGTCTTG
CCGAAGTCCCAGGCGGCAGCGGACCTGCTGGCTGTTACCGATGCGAAGGAGCTGTCCCGCGTGGTTGCTGCTGTCGG
TTTGGCGCAAAACCTGGCGGCACTGCGTGCCCTGGTGAGCGAGGGTATTCAAAAAGGTCACATGGCGTTGCAAGCGC
GTAGCCTGGCAATGACGGTCGGTGCAACCGGCAAAGAAGTGGAGGCGGTCGCCCAACAGCTGAAGCGCCAAAAGACC
ATGAACCAAGACCGCGCAATGGCCAATTCTGAATGATCTGCGCAAGCAATGAGAGGAGATAAAATATATGACCATCGG
CATCGACAAAATCAGCTTCTTCGTCCCACCGTACTACATCGATATGACTGCGCTGGCAGAAGCTCGTAACGTTGACC
CGGGTAAATTCCACATTGGCATTGGCCAGGATCAGATGGCAGTTAATCCGATTTCGCAGGATATCGTTACCTTTGCG
GCCAACGCGGCTGAGGCGATCCTGACCAAAGAGGATAAAGAGGCCATTGACATGGTCATCGTGGGTACGGAATCTAG
CATTGATGAATCCAAAGCAGCAGCCGTTGTTCTGCACCGTCTGATGGGTATCCAACCTTTCGCGCGTTCTTTCGAAA
TCAAAGAAGCGTGTTACGCGCAACGGCGGGTTTGCAGCTGGCTAAAAACCACGTTGCACTGCACCCAGACAAAAAG
GTGTTGGTTGTGGCGGCAGACATCGCGAAGTACGGCCTGAACAGCGGTGGCGAACCAACGCAGGGCGCTGGTGCAGT
GGCGATGCTGGTCGCGAGCGAACCGCGCATCCTGGCGCTGAAAGAAGATAATGTGATGTTGACTCAGGATATCTACG
ACTTCTGGCGTCCGACGGGCCATCCGTACCCGATGGTGGACGGTCCACTGTCGAACGAGACTTACATTCAGAGCTTT
GCACAAGTCTGGGATGAACACAAAAAGCGCACGGGTTTGGACTTCGCGGACTATGACGCCTTGCCGTTTCACATCCC
GTATACGAAGATGGGCAAAAAGGCACTGCTGGCCAAGATTAGCGACCAAACCGAGGCTGAGCAAGAGCGTATCTTGG
CCCGTTATGAAGAGAGCATTGTCTATTCTCCGCGTGGGTAATCTGTATACGGGCAGCCTGTATCTGGGCTTGATT
AGCCTGCTGGAGAACGCGACCACGCTGACCGCAGGTAATCAGATTGGTCTGTTTTCCTATGGTAGCGGTGCGGTGGC
GGAGTTTTTCACGGGCGAGCTGGTGGCGGGTTACCAAAATCATTTGCAAAAGGAAACCCATCTGGCGCTGTTGGACA
ATCGCACGGAACTGAGCATTGCAGAATATGAGGCGATGTTCGCGGAAACCCTGGATACCGATATTGACCAGACCCTG
GAGGATGAACTGAAGTACTCTATTAGCGCCATCAACAACACCGTGCGTAGCTACCGTAACTAAACGCGT
(SEQ ID NO: 7)
```

Fig. 23

```
ACGCGTGCTAGAGGCATCAAATAAAACGAAAGGCTCAGTCGAAAGACTGGGCCTTTCGTTTTATCTGTTGTTTGTCG
GTGAACGCTCTCCTGAGTAGGACAAATCCGCCGCCCTAGATCTCTAGATTCCCTATCAGTGATAGAGATTGACATCC
CTATCAGTGATAGAGATACTGAGCACATCAGCAGGACGCACTGACCTGTACAGAAGGAGATATACATATGATCATCG
AAACCCCATCCAAAGTAATCCTGTTCGGCGAGCACGCGGTTGTTTATGGTTACCGTGCCATCAGCATGGCAATTGAT
CTGACCAGCACCATTGAGATCAAGGAAACGCAAGAGGACGAAATCATCCTGAATCTGAACGATCTGAACAAATCGCT
GGGTCTGAATCTGAACGAAATCAAGAATATCAATCCGAACAATTTTGGCGACTTCAAGTATTGTCTGTGCGCTATCA
AGAACACCCTGGACTACCTGAATATCGAACCGAAAACTGGTTTTAAGATCAACATCAGCTCCAAAATCCCGATTAGC
TGTGGCCTGGGTTCTAGCGCGAGCATTACGATCGGCACGATTAAAGCGGTTTCTGGCTTCTACAATAAAGAGTTGAA
AGACGACGAAATCGCGAAGCTGGGCTACATGGTTGAGAAGGAAATCCAGGGTAAAGCATCCATCACGGATACCAGCA
CTATTACGTACAAAGGTATTCTGGAAATCAAGAATAACAAATTCCGCAAAATCAAAGGTGAGTTCGAGGAATTTCTG
AAGAACTGCAAATTTCTGATCGTTTATGCGGAGAAACGCAAGAAGAAAACCGCCGAATTGGTGAACGAAGTCGCAAA
AATCGAGAACAAAGATGAGATTTTCAAGGAAATCGATAAAGTGATTGACGAGGCGCTGAAGATTAAGAATAAAGAGG
ACTTTGGTAAGTTGATGACCAAAAATCACGAGCTGCTGAAGAAGCTGAACATTAGCACCCCGAAGCTGGACCGCATC
GTTGATATTGGCAACCGTTTTGGCTTCGGTGCTAAACTGACCGGCGCTGGCGGTGGTGGTTGCGTCATTATCCTGGT
TAACGAAGAGAAAGAAAGGAACTGCTGAAAGAGCTGAACAAAGAGGACGTACGCATTTTCAACTGTCGTATGATGA
ATTGAAGAAGGAGATATACCATGATCGAAGTAACTACCCCAGGCAAACTGTTCATCGCCGGCGAGTATGCAGTGGTT
GAGCCGGGTCACCCGGCGATTATTGTCGCGGTGGACCAGTTCGTCACGGTCACGGTAGAAGAAACCACCGATGAGGG
CAGCATCCAGAGCGCGCAATACAGCAGCCTGCCGATTCGTTGGACCCGTCGCAATGGTGAACTGGTACTGGATATCC
GTGAAAATCCGTTCCATTACGTTCTGGCCGCTATTCACCTGACCGAGAAGTATGCACAAGAACAGAATAAGGAACTG
AGCTTCTACCACCTGAAAGTGACCAGCGAGCTGGATTCGAGCAACGGCCGCAAATACGGTTTGGGCAGCAGCGGTGC
AGTCACCGTCGGTACGGTGAAGGCCCTGAATATCTTTTACGATCTGGGTCTGGAAAACGAGGAAATCTTTAAGCTGT
CCGCGCTGGCGCACCTGGCAGTGCAGGGTAATGGTAGCTGCGGTGACATCGCAGCGTCTTGTTACGGTGGCTGGATC
GCATTTAGCACTTTTGACCACGATTGGGTCAACCAGAAGGTCGCGACCGAGACTCTGACCGATCTGCTGGCTATGGA
CTGGCCGGAGCTGATGATTTTCCCTCTGAAAGTCCCGAAACAATTGCGTCTGCTGATTGGCTGGACGGGTTCGCCTG
CGAGCACCTCTGACCTGGTTGATCGCGTACACCAGTCTAAAGAAGAGAAACAAGCGCGTATGAGCAATTCCTGATG
AAATCCCGTCTGTGTGTCGAAACCATGATTAACGGTTTCAATACCGGCAAGATTAGCGTGATTCAAAAACAGATCAC
CAAGAACCGTCAACTGTTGGCAGAACTGAGCAGCCTGACGGGCGTTGTCATTGAAACCGAGGCGCTGAAAAACTTGT
GTGACCTGGCGGAGAGCTATACGGGTGCCGCTAAAAGCAGCGGTGCTGGTGGCGGCGACTGCGGTATTGTTATCTTC
CGCCAGAAGTCTGGTATCCTGCCGCTGATGACCGCGTGGGAGAAGGACGGCATCACGCCGCTGCCGTTGCACGTTTA
CACCTATGGTCAGAAAGAATGCAAAGAGAAACACGAGAGCAAGCGTTAAAGGAGGTATAAAAAATGACCGTCTACAC
CGCCAGCGTCACCGCACCAGTAAACATCGCGACGTTGAAGTACTGGGGTAAACGTGATACCAAGCTGAACTTGCCGA
CGAACAGCAGCATCAGCGTTACCCTGTCCCAGGACGATCTGCGTACGCTGACGAGCGCAGCTACTGCGCCGGAGTTC
GAACGTGACACCCTGTGGCTGAACGGCGAACCGCATAGCATTGACAACGAACGTACGCAAAACTGCCTGCGCGACCT
GCGCCAATTGCGCAAAGAAATGGAATCTAAAGATGCAAGCCTGCCTACCCTGAGCCAGTGGAAGCTGACACATTGTGA
GCGAGAACAATTTTCCGACGGCGGCAGGCCTGGCAAGCTCTGCCGCAGGCTTTGCAGCACTGGTCAGCGCCATCGCG
AAATTGTACCAATTGCCGCAATCCACCTCGGAGATTTCTCGCATCGCTCGTAAAGGCAGCGGCAGCGCCTGCCGCTC
TCTGTTTGGCGGTTATGTTGCCTGGGAAATGGGCAAGGCCGAGGACGGTCACGATTCGATGGCTGTCCAGATTGCCG
ACAGCAGCGATTGGCCGCAAATGAAGGCGTGCGTTCTGGTCTGGTGCGACATCAAGAAGGACGTGAGCAGCACCCAG
GGTATGCAACTGACGGTCGGCTACCGAGCGAGCTGTTCAAAGAGCGCATTGAGCACGTCGTTCCGAAGCGTTTCGAAGT
CATGCGCAAAGCGATCGTAGAGAAAGACTTTGCTACGTTTGCGAAAGAAACCATGATGGACTCCAATAGCTTCCACG
CGACCTGTCTGGATTCTTTTCCGCCGATCTTCTATATGAACGATACGAGCAAACGCATCATCTCCTGGTGTCACACG
ATCAATCAGTTTTATGGCGAAACCATTGTCGCATACACCTTCGATGCGGGTCCGAACGCAGTCCTGTACTACCTGGC
AGAAAACGAAAGCAAGCTGTTCGCCTTCATTTACAAACTGTTTGGCAGCGTGCCGGGTTGGGACAAAAAGTTCACGA
CGGAACAGCTGGAGGCATTTAACCACCAGTTCGAGAGCAGCAATTTCACCGCTCGTGAATTGGATCTGGAGCTGCAA
AAGGACGTGGCGCGTGTTATTCTGACCCAAGTTGGTTCTGGCCCGCAAGAAACGAACGAGTCTCTGATCGATGCGAA
AACCGGCCTGCCGAAGGAGTAGGAAGGAGATATAAAAATGCAAACCGAACACGTAATCCTGCTGAACGCACAAGGCG
TCCCGACGGGTACGCTGGAGAAATATGCAGCCCACACCGCTGACACCCGCTTGCACCTGGCTTTTAGCTCTTGGCTG
TTCAACGCAAAAGGTCAACTGCTGGTTACCCGCCGTGCACTGAGCAAGAAGGCGTGGCCGGGTGTCTGGACTAATAG
CGTGTGCGGTCACCCGCAACTGGGTGAAAGCAATGAGGACGCAGTGATTCGTCGTTGTCGTTATGAATTGGGTGTCG
AAATCACCCCGCCTGAAAGCATTTATCCGGACTTCCGTTACCGTGCCACCGATCCGACGCGGTATCGTTGAAAACGAA
GTTTGTCCGGTCTTTGCGGCCACGTACGACCAGCGCCGTAAATCAACGACGACGAGGTGATGGACTACCAGTGGTTG
TGATCTGCCGACGTTCTGCATGCGCATCGATGCCACCCCGTGGGCCTTTTCTCCGTGGATGGTGATGCAGGCGACCA
ACCGTGAGGCGCGTAAACGTTTGAGCGCGTTCACCCAACTGAAGTAACCATGGGCTAGAGGCATCAAATAAAACGAA
AGGCTCAGTCGAAAGACTGGGCCTTTCGTTTTATCTGTTGTTTGTCGGTGAACGCTCTCCTGAGTAGGACAAATCCG
CCGCCCTAGACCTAGG (SEQ ID NO: 8)
```

Fig. 24

SEQUENCE LISTING

```
<160> NUMBER OF SEQ ID NOS: 13

<210> SEQ ID NO 1
<211> LENGTH: 1235
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
aggaggtaaa acatatgcac caccatcatc accacatgcg ctttacgttg aaaaccaccg      60
ccatcgtgtc cgctgcggcg ttgctggcag gtttcggtcc gccaccgcgt gcggcggagc     120
tgccgccagg ccgtctggcg accaccgaag attacttcgc gcaacaagcg aaacaggcgg     180
tgacgccgga tgtgatggca caactggcct acatgaacta cattgacttc atcagcccgt     240
tctacagccg tggttgcagc tttgaagcgt gggagttgaa gcatacgccg caacgcgtca     300
ttaagtatag cattgcgttc tatgcatacg gtctggcgtc ggtcgcactg attgacccga     360
agctgcgtgc cctggcaggt cacgatctgg atatcgcggt gtctaaaatg aagtgcaagc     420
gtgtttgggg tgactgggaa gaggatggtt ttggcaccga cccgatcgag aaagagaaca     480
tcatgtacaa aggtcatctg aacctgatgt atggcctgta tcagctggtg acgggtagcc     540
gtcgctacga ggcagagcac gcgcacctga cccgtatcat ccatgacgag attgccgcta     600
atccgttcgc cggcatcgta tgtgaaccgg acaattactt tgtccagtgt aacagcgtcg     660
cgtacttgag cctgtgggtt tatgaccgtc tgcacggcac tgattatcgc gcagccaccc     720
gtgcttggtt ggatttcatt cagaaggacc tgatcgaccc ggagcgcggt gcattctacc     780
tgtcttacca cccggaaagc ggtgctgtta agccgtggat tagcgcgtat accactgcat     840
```

```
ggacgctggc catggttcac ggcatggatc cggcgtttag cgagcgctac tatccgcgct    900
tcaaacagac cttcgttgaa gtgtacgacg agggccgtaa agcccgggtt cgtgaaaccg    960
ccggtaccga cgacgccgac ggtggcgtgg gtctggcgag cgcgtttacg ctgttgttgg   1020
cacgtgagat gggcgatcag caactgtttg atcagctgct gaatcatctg gaaccgcctg   1080
ccaaaccgag cattgtcagc gcgtccctgc gttatgaaca ccctggctcc ctgctgtttg   1140
atgagctgct gttcctggct aaagttcatg caggttttgg tgcgctgctg cgtatgccgc   1200
caccggcagc gaagctggcg ggcaagtaac tcgag                              1235
```

<210> SEQ ID NO 2
<211> LENGTH: 1400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
aggaggtaaa acatatgcat catcaccacc accacatgga aaagatcgag gtaagcatta     60
acagcaaaca tacgattaaa ccgagcacga gctccacccc gttgcagccg tataagctga    120
ccctgctgga ccaactgacc ccaccggcat acgtcccaat cgtcttttc tatccgatta     180 cggatcacga cttcaatctg ccgcagacgc tggcagacct cgtcaagcc ctgtccgaaa     240 ccctgactct gtattacccg ctgagcggtc gtgtgaagaa taacttgtac attgacgact    300
tcgaagaggg cgttccgtac ctggaagcgc gtgtcaattg tgatatgacg gacttcctgc    360
gcctgcgtaa gattgagtgt ttgaacgagt tcgtgccgat taagccgttt agcatggaag    420
ccattagcga cgagcgttac ccgttgctgg gtgttcaagt caacgtgttc gatagcggta    480
tcgcgatcgg tgtttcggtt tctcataaac tgatcgacgg cggcaccgcg gactgcttcc    540
tgaaatcctg gggtgcggtt ttccgcggtt gccgcgagaa tatcatccac ccgagcctga    600
gcgaggcggc actgctgttc ccaccgcgcg atgatttgcc ggagaaatat gttgatcaga    660
tggaagccct gtggttcgcg ggtaaaaagg ttgcgacccg tcgctttgtc tttggtgtta    720
aggcgatcag cagcatccag gacgaggcaa agtctgaatc ggtgcctaag ccgtcccgtg    780
tgcacgcggt caccggcttt ctgtggaagc acctgattgc ggcaagccgt gctctgacct    840
ctggcaccac ctcgacgcgc ctgagcattg cggcacaggc cgttaatctg cgtacccgca    900
tgaacatgga aactgtgctg acaatgcga ccggcaacct gttttggtgg gcgcaggcta    960
ttctggagtt gagccacacc accccggaga tcagcgatct gaagctgtgc gatctggtga   1020
acttgttgaa tggcagcgtt aaacaatgca atggtgatta cttcgaaacg tttaaaggta   1080
aagagggcta tggccgtatg tgtgaatatc tggattttca gcgtacgatg agcagcatgg   1140
agccggcacc ggatatctac ctgtttagca gctggacgaa cttctttaac ccgctggact   1200
ttggttgggg tcgtaccagc tggatcggtg tcgcaggtaa gatcgagagc gccagctgca   1260
aattcattat tctggtgcct acccaatgtg gctctggtat cgaggcttgg gtgaacctgg   1320
aagaagagaa aatggccatg ctggaacaag acccgcattt cctggcgctg gctagcccga   1380
aaaccttgat ttaactcgag                                               1400
```

<210> SEQ ID NO 3
<211> LENGTH: 602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
attaaagagg agaaaatata atgacggcag tatgcctggt ccgccacggc gaaaccgatt      60
ggaacctgca acagaaatgc cagggtaaaa ccgatatccc gctgaatgcg acgggcgaac     120
gtcaggcccg tgaaacgggt gaatacgtca agactttag  ctgggacatc attgttacca     180
gcccgctgaa gcgcgccaag cgtacggctg agatcatcaa tgaatacctg catctgccga     240
tcgttgaaat ggacgacttt aaagagcgcg attatggcga tgctgagggt atgccgttgg     300
aggagcgcac caagcgttat ccggacaaca tttatccgaa catggagact ctggaagagc     360
tgacggaccg tttgatgggc ggtctggcaa aagtcaatca ggcatacccg aacaaaaagg     420
tgctgatcgt tgcacatggt gcggcaattc acgcgctgct gacggagatt tctggtggtg     480
acccggagct gcaaagcacc cgtctggtca atgcgtgttt gtcgaatatt gaatttgcgg     540
aagaaaagtg gcgtatcaaa gactacaaca ttaactccca tctgagcggt ttcatcaaat     600
aa                                                                    602
```

<210> SEQ ID NO 4
<211> LENGTH: 2494
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
ggtaccttaa ttaatataag gaggtaaaac atatgaacgt tgaaaccaaa cacacgcgca     60
cgatgggtga cattttttgta caacatagcc agaaactgga actgctgaaa accgtcctgc    120
gtaacgtcgc tgagctggac gcactggaag gcttgaacat gattgacgcg gtgcagcgtt    180
tgggtatcga ctacaatttt cagcgtgaga ttgacgagat tctgcacaag cagatgagca    240
tcgtcagcgc gcgtgacgac ttgcacgagg ttgcgctgcg cttccgtctg ctgcgccagc    300
atggctattt cgtcccagag gatgttttca caatttcaa  ggactcgaaa ggtacgttca    360
aacaggtgct gggtgaggac atcaagggcc tgatgagcct gtacgaggcg agccaactgg    420
gcaccgaggg cgaggacatt ctggttgaag cggagaagtt cagcggccac ttgctgaaaa    480
cgagcctgag ccacctggat catcatcgtg tgcgtattgt ggcgaatacc ttgcgcaatc    540
cgcaccacaa aagcctggcg cctttcatgg cacgtaactt tttcgttacg agccaagcta    600
ctaatagctg gctgaatctg ttgaaagagg tcgccaagac ggacttcaat atggtgcgct    660
ctctgcacca aaatgagatt gttcagatgt ccaaatggtg gaaagagctg ggcctggcca    720
agagctgaa  gttcgcccgt gaccagccgc tgaagtggta catttggagc atggcgtgcc    780
tgaccgatcc gaaactgagc gaagagcgtg ttgagctgac gaagccaatc agctttgttt    840
acttgattga cgatatcttt gacgtttacg gcacgctgga cgacctgatc ctgtttaccg    900
aggccgttaa tcgttgggag atcacggcga tcgaccactt gcctgactat atgaagattt    960
gttttaaggc attgtacgat atgaccaatg agtttagcag caaggtctat ctgaaacatg   1020
gctggaaccc gctgcaaagc ctgaaaatca gctgggcgag cttgtgtaac gcattcctgg   1080
tcgaggccaa gtggtttgcg agcggtaagc tgccgaaaag cgaagagtat ttgaagaatg   1140
gtattgtgag cagcggtgtt aatgtggtgc tggtgcacat gttttttcctg ctgggtcaaa   1200
acatcacccg caaatctgtc gagctgctga acgaaactcc ggcgatcatt agctctagcg   1260
ctgcgatcct gcgcctgtgg gatgatttgg gtagcgcgaa ggacgagaat caagacggta   1320
```

| | | | |
|---|---|---|---|
| acgatggtag | ctatgttcgt | tgctacctgg aagaacacga aggttgcagc atcgaagaag | 1380 |
| cgcgcgagaa | aaccatcaac | atgattagcg atgagtggaa gaagttgaat cgcgagttgc | 1440 |
| tgagcccgaa | cccgttccca | gcaagcttca ccctggcgag cctgaacctg cacgtatga | 1500 |
| tcccgctgat | gtactcctac | gacggtaatc agtgcctgcc ttccctgaaa gagtatatga | 1560 |
| agctgatgct | gtacgaaacc | gtcagcatgt gatgaggaat aaaattatgc tgcgtagcct | 1620 |
| gctgcgtggc | ctgacccact | ttccgcgtgt gaactccgct caacaaccgt cgtgcgccca | 1680 |
| tgcccgcctg | caatttcgtc | cgcgcagcat gcagctgctg ccgaagatc gtaccgacca | 1740 |
| catgcgtggt | gctagtacgt | gggcggcgg tcaatcccaa gatgaactga tgctgaaaga | 1800 |
| cgaatgcatt | ctggtcgatg | cggatgacaa catcaccggt catgtgagca actggaatg | 1860 |
| tcataagttt | ctgccgcacc | agccggcggg tctgctgcac cgtgcattct ctgttttct | 1920 |
| gttcgatgac | cagggtcgcc | tgctgctgca gcaacgtgcc cgcagcaaga ttacctttcc | 1980 |
| gtctgtttgg | accaatacgt | gctgttcaca tccgctcac ggccagaccc cggatgaagt | 2040 |
| ggatcagctg | tcgcaagtgg | ctgatggcac ggttccgggt gcaaaagcgg cggcaattcg | 2100 |
| taagctggaa | catgaactgg | gtatcccggc acaccagctg ccggcaagtg catttcgttt | 2160 |
| cctgacccgc | ctgcattatt | gtgctgccga tgttcagccg gcggcaaccc aatcagccct | 2220 |
| gtggggcgaa | cacgaaatgg | attacattct gttcatccgt gctaacgtga ccctggcgcc | 2280 |
| gaatccggat | gaagtggacg | aagttcgtta tgtcacgcag gaagaactgc gccagatgat | 2340 |
| gcaaccggat | aacggtctgc | aatggtcccc gtggtttcgc attatcgctg cgcgtttcct | 2400 |
| ggaacgttgg | tgggccgatc | tggacgcagc actgaacacc gataaacacg aagactgggg | 2460 |
| caccgtccat | cacatcaacg | aagcataacc atgg | 2494 |

<210> SEQ ID NO 5
<211> LENGTH: 3228
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | |
|---|---|---|---|
| ggatcctccc | tatcagtgat | agagattgac atccctatca gtgatagaga tactgagcac | 60 |
| atcagcagga | cgcactgacc | ggtacctttg aattccccac gcgtagatct ctagatgtac | 120 |
| accatgggct | agaggcatca | aataaaacga aaggctcagt cgaaagactg gcctttcgt | 180 |
| tttatctgtt | gtttgtcggt | gaacgctctc ctgagtagga caaatccgcc gccctagacc | 240 |
| taggcgttcg | gctgcggcga | gcggtatcag ctcactcaaa ggcggtaata cggttatcca | 300 |
| cagaatcagg | ggataacgca | ggaaagaaca tgtgagcaaa aggccagcaa aaggccagga | 360 |
| accgtaaaaa | cgcgctagcg | gagtgtatac tggcttacta tgttggcact gatgagggtg | 420 |
| tcagtgaagt | gcttcatgtg | gcaggagaaa aaaggctgca ccggtgcgtc agcagaatat | 480 |
| gtgatacagg | atatattccg | cttcctcgct cactgactcg ctacgctcgg tcgttcgact | 540 |
| gcggcgagcg | gaaatggctt | acgaacgggg cggagatttc ctggaagatg ccaggaagat | 600 |
| acttaacagg | gaagtgagag | ggccgcggca aagccgtttt tccataggct ccgccccct | 660 |
| gacaagcatc | acgaaatctg | acgctcaaat cagtggtggc gaaacccgac aggactataa | 720 |
| agataccagg | cgtttccccc | tggcggctcc ctcgtgcgct ctcctgttcc tgcctttcgg | 780 |
| tttaccggtg | tcattccgct | gttatggccg cgtttgtctc attccacgcc tgacactcag | 840 |

```
ttccgggtag gcagttcgct ccaagctgga ctgtatgcac gaaccccccg ttcagtccga    900
ccgctgcgcc ttatccggta actatcgtct tgagtccaac ccggaaagac atgcaaaagc    960
accactggca gcagccactg gtaattgatt tagaggagtt agtcttgaag tcatgcgccg   1020
gttaaggcta aactgaaagg acaagttttg gtgactgcgc tcctccaagc cagttacctc   1080
ggttcaaaga gttggtagct cagagaacct tcgaaaaacc gccctgcaag gcggtttttt   1140
cgttttcaga gcaagagatt acgcgcagac caaaacgatc tcaagaagat catcttatta   1200
agtggcctaa ctacggctac actagaagga cagtatttgg tatctgcgct ctgctgaagc   1260
cagttacctt cggaaaaaga gttggtagct cttgatccgg caaacaaacc accgctggta   1320
gcggtggttt ttttgtttgc aagcagcaga ttacgcgcag aaaaaaagga tctcaagaag   1380
atcctttgat cttttctacg gggtctgacg ctcagtggaa cgaaaactca cgttaaggga   1440
ttttggtcat gactagtgct tggattctca ccaataaaaa acgcccggcg caaccgagc    1500
gttctgaaca atccagatg gagttctgag gtcattactg gatctatcaa caggagtcca    1560
agcgagctcg atatcaaatt acgccccgcc ctgccactca tcgcagtact gttgtaattc   1620
attaagcatt ctgccgacat ggaagccatc acagacggca tgatgaacct gaatcgccag   1680
cggcatcagc accttgtcgc cttgcgtata atatttgccc atcgtgaaaa cgggggcgaa    1740
gaagttgtcc atattggcca cgtttaaatc aaaactggtg aaactcaccc agggattggc   1800
tgagacgaaa aacatattct caataaaccc tttagggaaa taggccaggt tttcaccgta   1860
acacgccaca tcttgcgaat atatgtgtag aaactgccgg aaatcgtcgt ggtattcact   1920
ccagagcgat gaaaacgttt cagtttgctc atggaaaacg gtgtaacaag ggtgaacact   1980
atcccatatc accagctcac cgtctttcat tgccatacgg aactccggat gagcattcat   2040
caggcgggca agaatgtgaa taaaggccgg ataaaacttg tgcttatttt tctttacggt   2100
ctttaaaaag gccgtaatat ccagctgaac ggtctggtta taggtacatt gagcaactga   2160
ctgaaatgcc tcaaaatgtt ctttacgatg ccattgggat atatcaacgg tggtatatcc   2220
agtgattttt ttctccattt tagcttcctt agctcctgaa atctcgata actcaaaaaa   2280
tacgcccggt agtgatctta tttcattatg gtgaaagttg gaacctctta cgtgccgatc   2340
aacgtctcat tttcgccaga tatcgacgtc gtcatcaaac ctgtcgcgca ctctaggcta   2400
ctcagctact agaaagctta agacccactt tcacatttaa gttgttttc taatccgcag    2460
atgatcaatt caaggccgaa taagaaggct ggctctgcac cttggtgatc aaataattcg   2520
atagcttgtc gtaataatgg cggcatacta tcagtagtag gtgtttccct tcttctttta   2580
gcgacttgat gctcttgatc ttccaatacg caacctaaag taaaatgccc cacagcgctg   2640
agtgcatata atgcattctc tagtgaaaaa ccttgttggc ataaaaaggc taattgattt   2700
tcgagagttt catactgttt ttctgtaggc cgtgtaccta aatgtacttt tgctccatcg   2760
cgatgactta gtaaagcaca tctaaaactt ttagccttat tacgtaaaaa atcttgccag   2820
ctttccccctt ctaaagggca aaagtgagta tggtgcctat ctaacatctc aatggctaag   2880
gcgtcgagca aagcccgctt atttttaca tgccaataca atgtaggctg ctctacacct   2940
agcttctggg cgagtttacg ggttgttaaa ccttcgattc cgacctcatt aagcagctct   3000
aatgcgctgt taatcacttt actttttatct aatcttaaca tgtgaatacg gggcgggatt   3060
tcatggatat gtttctttct gcgagaacca gccatattta aactcttctc tcaaatttat   3120
gaatctatta tacagaaaaa ttttcctgaa agcaaataaa tttttttatga tttccctcga   3180
caattcgcgc taacttacat taattgcgtt gcgctcactg cccgcttt                3228
```

<210> SEQ ID NO 6
<211> LENGTH: 4236
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

| | | | | | | |
|---|---|---|---|---|---|---|
| ggatcctccc | tatcagtgat | agagattgac | atccctatca | gtgatagaga | tactgagcac | 60 |
| atcagcagga | cgcactgacc | ggtacctttg | aattccccac | gcgtagatct | ctagatgtac | 120 |
| accatgggct | agaggcatca | aataaaacga | aaggctcagt | cgaaagactg | ggcctttcgt | 180 |
| tttatctgtt | gtttgtcggt | gaacgctctc | ctgagtagga | caaatccgcc | gccctagacc | 240 |
| tagggtacgg | gttttgctgc | ccgcaaacgg | gctgttctgg | tgttgctagt | ttgttatcag | 300 |
| aatcgcagat | ccggcttcag | gtttccggc | tgaaagcgct | atttcttcca | gaattgccat | 360 |
| gattttttcc | ccacgggagg | cgtcactggc | tcccgtgttg | tcggcagctt | tgattcgata | 420 |
| agcagcatcg | cctgtttcag | gctgtctatg | tgtgactgtt | gagctgtaac | aagttgtctc | 480 |
| aggtgttcaa | tttcatgttc | tagttgcttt | gttttactgg | tttcacctgt | tctattaggt | 540 |
| gttacatgct | gttcatctgt | tacattgtcg | atctgttcat | ggtgaacagc | tttaaatgca | 600 |
| ccaaaaactc | gtaaaagctc | tgatgtatct | atctttttta | caccgttttc | atctgtgcat | 660 |
| atggacagtt | ttcccttga | tatctaacgg | tgaacagttg | ttctactttt | gtttgttagt | 720 |
| cttgatgctt | cactgataga | tacaagagcc | ataagaacct | cagatccttc | cgtatttagc | 780 |
| cagtatgttc | tctagtgtgg | ttcgttgttt | ttgcgtgagc | catgagaacg | aaccattgag | 840 |
| atcatgctta | ctttgcatgt | cactcaaaaa | ttttgcctca | aaactggtga | gctgaatttt | 900 |
| tgcagttaaa | gcatcgtgta | gtgttttct | tagtccgtta | cgtaggtagg | aatctgatgt | 960 |
| aatggttgtt | ggtattttgt | caccattcat | tttatctgg | ttgttctcaa | gttcggttac | 1020 |
| gagatccatt | tgtctatcta | gttcaacttg | gaaaatcaac | gtatcagtcg | gcggcctcg | 1080 |
| cttatcaacc | accaatttca | tattgctgta | agtgtttaaa | tctttactta | ttggtttcaa | 1140 |
| aacccattgg | ttaagccttt | taaactcatg | gtagttattt | tcaagcatta | acatgaactt | 1200 |
| aaattcatca | aggctaatct | ctatatttgc | cttgtgagtt | ttcttttgtg | ttagttcttt | 1260 |
| taataaccac | tcataaatcc | tcatagagta | tttgttttca | aaagacttaa | catgttccag | 1320 |
| attatatttt | atgaattttt | ttaactggaa | aagataaggc | aatatctctt | cactaaaaac | 1380 |
| taattctaat | ttttcgcttg | agaacttggc | atagtttgtc | cactggaaaa | tctcaaagcc | 1440 |
| tttaaccaaa | ggattcctga | tttccacagt | tctcgtcatc | agctctctgg | ttgctttagc | 1500 |
| taatacacca | taagcatttt | ccctactgat | gttcatcatc | tgagcgtatt | ggttataagt | 1560 |
| gaacgatacc | gtccgttctt | tccttgtagg | gttttcaatc | gtggggttga | gtagtgccac | 1620 |
| acagcataaa | attagcttgg | tttcatgctc | cgttaagtca | tagcgactaa | tcgctagttc | 1680 |
| atttgctttg | aaaacaacta | attcagacat | acatctcaat | tggtctaggt | gatttaatc | 1740 |
| actataccaa | ttgagatggg | ctagtcaatg | ataattacta | gtccttttcc | cgggagatct | 1800 |
| gggtatctgt | aaattctgct | agacctttgc | tggaaaactt | gtaaattctg | ctagaccctc | 1860 |
| tgtaaattcc | gctagacctt | tgtgtgtttt | ttttgtttat | attcaagtgg | ttataattta | 1920 |
| tagaataaag | aaagaataaa | aaagataaa | aagaatagat | cccagccctg | tgtataactc | 1980 |
| actactttag | tcagttccgc | agtattacaa | aaggatgtcg | caaacgctgt | ttgctcctct | 2040 |
| acaaaacaga | ccttaaaacc | ctaaaggctt | aagtagcacc | ctcgcaagct | cgggcaaatc | 2100 |

```
gctgaatatt cctttgtcct ccgaccatca ggcacctgag tcgctgtctt tttcgtgaca    2160
ttcagttcgc tgcgctcacg gctctggcag tgaatgggg  taaatggcac tacaggcgcc    2220
ttttatggat tcatgcaagg aaactaccca taatacaaga aaagcccgtc acgggcttct    2280
cagggcgttt tatggcgggt ctgctatgtg gtgctatctg actttttgct gttcagcagt    2340
tcctgccctc tgattttcca gtctgaccac ttcggattat cccgtgacag gtcattcaga    2400
ctggctaatg cacccagtaa ggcagcggta tcatcaacag gcttacccgt cttactgtcc    2460
ctagtgcttg gattctcacc aataaaaaac gcccggcggc aaccgagcgt tctgaacaaa    2520
tccagatgga gttctgaggt cattactgga tctatcaaca ggagtccaag cgagctcgat    2580
atcaaattac gccccgccct gccactcatc gcagtactgt tgtaattcat taagcattct    2640
gccgacatgg aagccatcac agacggcatg atgaacctga tcgccagcg  gcatcagcac    2700
cttgtcgcct tgcgtataat atttgcccat cgtgaaaacg ggggcgaaga agttgtccat    2760
attggccacg tttaaatcaa aactggtgaa actcacccag ggattggctg agacgaaaaa    2820
catattctca ataaacccctt tagggaaata ggccaggttt tcaccgtaac acgccacatc    2880
ttgcgaatat atgtgtagaa actgccggaa atcgtcgtgg tattcactcc agagcgatga    2940
aaacgtttca gtttgctcat ggaaaacggt gtaacaaggg tgaacactat cccatatcac    3000
cagctcaccg tctttcattg ccatacgaaa ctccggatga gcattcatca ggcgggcaag    3060
aatgtgaata aaggccggat aaaacttgtg cttattttc  tttacggtct ttaaaaaggc    3120
cgtaatatcc agctgaacgg tctggttata ggtacattga gcaactgact gaaatgcctc    3180
aaaatgttct ttacgatgcc attgggatat atcaacggtg gtatatccag tgatttttt     3240
ctccatttta gcttccttag ctcctgaaaa tctcgataac tcaaaaaata cgcccggtag    3300
tgatcttatt tcattatggt gaaagttgga acctcttacg tgccgatcaa cgtctcattt    3360
tcgccagata tcgacgtcgt catcaaacct gtcgcgcact ctaggctact cagctactag    3420
aaagcttaag acccactttc acatttaagt tgttttttcta atccgcagat gatcaattca    3480
aggccgaata agaaggctgg ctctgcacct tggtgatcaa ataattcgat agcttgtcgt    3540
aataatggcg gcatactatc agtagtaggt gttttccctt cttctttagc gacttgatgc    3600
tcttgatctt ccaatacgca acctaaagta aaatgcccca cagcgctgag tgcatataat    3660
gcattctcta gtgaaaaacc ttgttggcat aaaaaggcta attgattttc gagagtttca    3720
tactgttttt ctgtaggccg tgtacctaaa tgtacttttg ctccatcgcg atgacttagt    3780
aaagcacatc taaaactttt agccttatta cgtaaaaaat cttgccagct ttccccttct    3840
aaagggcaaa agtgagtatg gtgcctatct aacatctcaa tggctaaggc gtcgagcaaa    3900
gcccgcttat ttttacatg  ccaatacaat gtaggctgct ctacacctag cttctgggcg    3960
agttacggg  ttgttaaacc ttcgattccg acctcattaa gcagctctaa tgcgctgtta    4020
atcactttac tttatctaa  tcttaacatg tgaatacggg gcgggatttc atggatatgt    4080
ttctttctgc gagaaccagc catatttaaa ctcttctctc aaatttatga atctattata    4140
cagaaaaatt ttcctgaaag caaataaatt ttttatgatt tccctcgaca attcgcgcta    4200
acttacatta attgcgttgc gctcactgcc cgcttt                              4236
```

<210> SEQ ID NO 7
<211> LENGTH: 3611
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
ggtaccatta aagaggagaa aatataatga aaactgtagt aatcatcgac gccctgcgca      60
cgccaatcgg caagtataag ggttctctga gccaagttag cgcagtcgat ctgggcaccc     120
atgtcacgac ccagttgctg aagcgtcatt ccaccatcag cgaggaaatt gatcaggtga     180
tcttcggtaa cgtcctgcaa gccggcaatg gtcagaaccc tgcgcgtcag attgcgatta     240
actctggctt gagccacgag atcccggcta tgacggtgaa tgaggtttgt ggcagcggta     300
tgaaggcggt tatcttggca aaacagctga tccagttggg tgaggccgag gtactgattg     360
cgggtggtat cgaaaacatg agccaggcgc aaaattgca acgttttaac tatgaaactg     420
aaagctatga cgcgccgttt ccagcatga tgtacgacgg tctgaccgat gcgttcagcg     480
gtcaggcgat gggcctgact gcggagaatg tggcggagaa gtaccacgtc actcgtgaag     540
aacaagacca gtttagcgtg cattcccagc tgaaagcggc gcaagcacaa gcagagggta     600
tcttcgcaga cgaaatcgcg ccgttggagg tgagcggcac gctggttgag aaagatgagg     660
gtatccgccc taattctagc gtggaaaagc tgggtactct gaaaaccgtt ttcaaagagg     720
acggtacggt tacggccggt aacgcgagca ccatcaatga tggtgcgagc gccctgatta     780
tcgcaagcca ggagtacgca gaggctcacg gtctgccgta cctggcgatt atccgtgaca     840
gcgttgaagt gggtatcgat ccggcatata tgggtatcag cccgattaag gcaattcaga     900
aattgctggc ccgtaaccag ctgaccacgg aggagattga tctgtacgag attaacgagg     960
cgtttgcagc aactagcatc gttgtgcagc gtgagttggc cctgccggag gagaaagtta    1020
acatttacgg tggcggtatc agcttgggtc atgcaatcgg cgccacgggc gctcgtctgc    1080
tgaccccct gagctaccaa ctgaatcaga aggagaagaa atacggcgtt gccagcctgt    1140
gcattggcgg tggcctgggt ctggccatgc tgttggaacg tccgcaacag aagaagaatt    1200
cacgttttta ccaaatgagc ccggaggagc gtttggccag cctgctgaat gagggtcaga    1260
ttagcgcgga taccaagaaa gaatttgaaa acaccgcgct gagcagccag attgctaatc    1320
acatgattga gaaccagatc agcgaaaccg aagtgccgat gggtgttggc ctgcacctga    1380
cggttgatga aaccgattac ctggttccga tggcaaccga agaacctagc gttattgcag    1440
cactgagcaa cggtgcaaag atcgctcagg cttcaaaac ggtcaatcag cagcgtctga    1500
tgcgtggcca aattgtcttt tatgatgtgg cagacccgga gtccttgatc gacaagctgc    1560
aagtacgtga ggcggaagtt ttccaacagg cggagctgag ctatccgagc atcgtcaagc    1620
gcggtggtgg tctgcgtgac ctgcaatacc gcacgtttga tgagagcttt gttagcgtgg    1680
actttctggt ggacgtgaag gacgcgatgg gtgccaatat cgttaatgca atgctggagg    1740
gtgtggcgga actgtttcgc gaatggttcg cagaacaaaa gattctgttc agcattttga    1800
gcaactacgc caccgaatcg gtagttacga tgaaaaccgc gattccagtg tctcgtctga    1860
gcaagggtag caatggtcgt gaaatcgccg agaaaattgt gctggccagc cgctacgcga    1920
gcctggaccc gtatcgcgcg gttacccaca taagggtat catgaatggc attgaagcgg    1980
tcgttctggc cacgggcaat gacacccgtg cggtgagcgc ttcctgccac gcatttgctg    2040
ttaaagaggg ccgttaccag ggcctgacct cgtggaccct ggatggtgag caactgatcg    2100
gcgagatcag cgttccgttg gcactggcca ccgtgggtgg tgcgaccaaa gtcttgccga    2160
agtcccaggc ggcagcggac ctgctggctg ttaccgatgc gaaggagctg tcccgcgtgg    2220
ttgctgctgt cggttttggcg caaaacctgg cggcactgcg tgccctggtg agcgagggta    2280
```

```
ttcaaaaagg tcacatggcg ttgcaagcgc gtagcctggc aatgacggtc ggtgcaaccg   2340
gcaaagaagt ggaggcggtc gcccaacagc tgaagcgcca aaagaccatg aaccaagacc   2400
gcgcaatggc aattctgaat gatctgcgca agcaatgaga ggagataaaa tatatgacca   2460
tcggcatcga caaaatcagc ttcttcgtcc caccgtacta catcgatatg actgcgctgg   2520
cagaagctcg taacgttgac ccgggtaaat tccacattgg cattggccag gatcagatgg   2580
cagttaatcc gatttcgcag gatatcgtta cctttgcggc aacgcggct gaggcgatcc     2640 tgaccaaaga ggataaagag gccattgaca tggtcatcgt gggtacggaa tctagcattg   2700
atgaatccaa agcagcagcc gttgttctgc accgtctgat gggtatccaa cctttcgcgc   2760
gttctttcga aatcaaagaa gcgtgttacg gcgcaacggc gggtttgcag ctggctaaaa   2820
accacgttgc actgcaccca gacaaaaagg tgttggttgt ggcggcagac atcgcgaagt   2880
acggcctgaa cagcggtggc gaaccaacgc agggcgctgg tgcagtggcg atgctggtcg   2940
cgagcgaacc gcgcatcctg cgcctgaaag aagataatgt gatgttgact caggatatct   3000
acgacttctg gcgtccgacg ggccatccgt acccgatggt ggacggtcca ctgtcgaacg   3060
agacttacat tcagagcttt gcacaagtct gggatgaaca caaaaagcgc acgggtttgg   3120
acttcgcgga ctatgacgcc ttggcgtttc acatcccgta tacgaagatg ggcaaaaagg   3180
cactgctggc caagattagc gaccaaaccg aggctgagca agagcgtatc ttggcccgtt   3240
atgaagagag cattgtctat tctcgccgcg tgggtaatct gtatacgggc agcctgtatc   3300
tgggcttgat tagcctgctg gagaacgcga ccacgctgac cgcaggtaat cagattggtc   3360
tgttttccta tggtagcggt gcggtggcgg agttttttcac gggcgagctg gtggcgggtt   3420
accaaaatca tttgcaaaag gaaacccatc tggcgctgtt ggacaatcgc acggaactga   3480
gcattgcaga atatgaggcg atgttcgcgg aaaccctgga taccgatatt gaccagaccc   3540
tggaggatga actgaagtac tctattagcg ccatcaacaa caccgtgcgt agctaccgta   3600
actaaacgcg t                                                       3611
```

<210> SEQ ID NO 8
<211> LENGTH: 4174
<212> TYPE: DNA
<213> ORGANISM: Artificial Sequence
<220> FEATURE:
<223> OTHER INFORMATION: Description of Artificial Sequence: Synthetic
  polynucleotide

<400> SEQUENCE: 8

```
acgcgtgcta gaggcatcaa ataaaacgaa aggctcagtc gaaagactgg gcctttcgtt   60
ttatctgttg tttgtcggtg aacgctctcc tgagtaggac aaatccgccg ccctagatct   120
ctagattccc tatcagtgat agagattgac atccctatca gtgatagaga tactgagcac   180
atcagcagga cgcactgacc tgtacagaag gagatataca tatgatcatc gaaaccccat   240
ccaaagtaat cctgttcggc gagcacgcgg ttgtttatgg ttaccgtgcc atcagcatgg   300
caattgatct gaccagcacc attgagatca aggaaacgca agaggacgaa atcatcctga   360
atctgaacga tctgaacaaa tcgctgggtc tgaatctgaa cgaaatcaag aatatcaatc   420
cgaacaattt tggcgacttc aagtattgtc tgtgcgctat caagaacacc ctggactacc   480
tgaatatcga accgaaaact ggttttaaga tcaacatcag ctccaaaatc ccgattagct   540
gtggcctggg ttctagcgcg agcattacga tcggcacgat taaagcggtt tctggcttct   600
acaataaaga gttgaaagac gacgaaatcg cgaagctggg ctacatggtt gagaaggaaa   660
tccagggtaa agcatccatc acggatacca gcactattac gtacaaaggt attctggaaa   720
```

```
tcaagaataa caaattccgc aaaatcaaag gtgagttcga ggaatttctg aagaactgca      780
aatttctgat cgtttatgcg gagaaacgca agaagaaaac cgccgaattg gtgaacgaag      840
tcgcaaaaat cgagaacaaa gatgagattt tcaaggaaat cgataaagtg attgacgagg      900
cgctgaagat taagaataaa gaggactttg gtaagttgat gaccaaaaat cacgagctgc      960
tgaagaagct gaacattagc accccgaagc tggaccgcat cgttgatatt ggcaaccgtt     1020
ttggcttcgg tgctaaactg accggcgctg gcggtggtgg ttgcgtcatt atcctggtta     1080
acgaagagaa agaaaaggaa ctgctgaaag agctgaacaa agaggacgta cgcatttttca    1140 actgtcgtat gatgaattga agaaggagat ataccatgat cgaagtaact accccaggca     1200
aactgttcat cgccggcgag tatgcagtgg ttgagccggg tcacccggcg attattgtcg     1260
cggtggacca gttcgtcacg gtcacggtag aagaaaccac cgatgagggc agcatccaga     1320
gcgcgcaata cagcagcctg ccgattcgtt ggacccgtcg caatggtgaa ctggtactgg     1380
atatccgtga aaatccgttc cattacgttc tggccgctat tcacctgacc gagaagtatg     1440
cacaagaaca gaataaggaa ctgagcttct accacctgaa agtgaccagc gagctggatt     1500
cgagcaacgg ccgcaaatac ggtttgggca gcagcggtgc agtcaccgtc ggtacggtga     1560
aggccctgaa tatcttttac gatctgggtc tggaaaacga ggaaatcttt aagctgtccg     1620
cgctggcgca cctggcagtg cagggtaatg gtagctgcgg tgacatcgca gcgtcttgtt     1680
acggtggctg gatcgcattt agcactttg accacgattg ggtcaaccag aaggtcgcga     1740
ccgagactct gaccgatctg ctggctatgg actggccgga gctgatgatt ttccctctga     1800
aagtcccgaa acaattgcgt ctgctgattg gctggacggg ttcgcctgcg agcacctctg     1860
acctggttga tcgcgtacac cagtctaaag aagagaaaca agcggcgtat gagcaattcc     1920
tgatgaaatc ccgtctgtgt gtcgaaacca tgattaacgg tttcaatacc ggcaagatta     1980
gcgtgattca aaaacagatc accaagaacc gtcaactgtt ggcagaactg agcagcctga     2040
cgggcgttgt cattgaaacc gaggcgctga aaaacttgtg tgacctggcg gagagctata     2100
cgggtgccgc taaaagcagc ggtgctggtg cggcgactg cggtattgtt atcttccgcc     2160
agaagtctgg tatcctgccg ctgatgaccg cgtgggagaa ggacggcatc acgccgctgc     2220
cgttgcacgt ttacacctat ggtcagaaag aatgcaaaga gaaacacgag agcaagcgtt     2280
aaaggaggta taaaaatga ccgtctacac cgccagcgtc accgcaccag taaacatcgc     2340
gacgttgaag tactgggggta acgtgatac caagctgaac ttgccgacga acagcagcat    2400
cagcgttacc ctgtcccagg acgatctgcg tacgctgacg agcgcagcta ctgcgccgga     2460
gttcgaacgt gacaccctgt ggctgaacgg cgaaccgcat agcattgaca cgaacgtac     2520 gcaaaactgc ctgcgcgacc tgcgccaatt gcgcaaagaa atggaatcta agatgcaag     2580 cctgcctacc ctgagccagt ggaagctgca cattgtgagc gagaacaatt ttccgacggc     2640
ggcaggcctg gcaagctctg ccgcaggctt tgcagcactg gtcagcgcca tcgcgaaatt     2700
gtaccaattg ccgcaatcca cctcggagat ttctcgcatc gctcgtaaag cagcggcag     2760 cgcctgccgc tctctgtttg gcggttatgt tgcctgggaa atgggcaagg ccgaggacgg     2820
tcacgattcg atggctgtcc agattgccga cagcagcgat tggccgcaaa tgaaggcgtg     2880
cgttctggtc gtgtccgaca tcaagaagga cgtgagcagc acccagggta tgcaactgac     2940
ggtcgctacc agcagctgt tcaaagagcg cattgagcac gtcgttccga agcgtttcga     3000
agtcatgcgc aaagcgatcg tagagaaaga ctttgctacg tttgcgaaag aaaccatgat     3060
ggactccaat agcttccacg cgacctgtct ggattctttt ccgccgatct tctatatgaa     3120
```

```
cgatacgagc aaacgcatca tctcctggtg tcacacgatc aatcagtttt atggcgaaac   3180
cattgtcgca tacaccttcg atgcgggtcc gaacgcagtc ctgtactacc tggcagaaaa   3240
cgaaagcaag ctgttcgcct tcatttacaa actgtttggc agcgtgccgg gttgggacaa   3300
aaagttcacg acggaacagc tggaggcatt taaccaccag ttcgagagca gcaatttcac   3360
cgctcgtgaa ttggatctgg agctgcaaaa ggacgtggcg cgtgttattc tgacccaagt   3420
tggttctggc ccgcaagaaa cgaacgagtc tctgatcgat gcgaaaaccg gcctgccgaa   3480
ggagtaggaa ggagatataa aaatgcaaac cgaacacgta atcctgctga acgcacaagg   3540
cgtcccgacg ggtacgctgg agaaatatgc agcccacacc gctgacaccc gcttgcacct   3600
ggcttttagc tcttggctgt tcaacgcaaa aggtcaactg ctggttaccc gccgtgcact   3660
gagcaagaag gcgtggccgg tgtctggac  taatagcgtg tgcggtcacc cgcaactggg   3720
tgaaagcaat gaggacgcag tgattcgtcg ttgtcgttat gaattgggtg tcgaaatcac   3780
cccgcctgaa agcatttatc cggacttccg ttaccgtgcc accgatccga gcggtatcgt   3840
tgaaaacgaa gtttgtccgg tctttgcggc acgtacgacc agcgcgctgc aaatcaacga   3900
cgacgaggtg atggactacc agtggtgtga tctggccgac gttctgcatg catcgatgc    3960 caccccgtgg gccttttctc cgtggatggt gatgcaggcg accaaccgtg aggcgcgtaa   4020
acgtttgagc gcgttcaccc aactgaagta accatgggct agaggcatca aataaaacga   4080
aaggctcagt cgaaagactg gcctttcgt  tttatctgtt gtttgtcggt gaacgctctc   4140
ctgagtagga caaatccgcc gccctagacc tagg                               4174
```

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgtaactaa acgcgaaggg aatatcatgc gaattgg                           37

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctagagatct acgcgtcagg gttacagagc tttc                              34

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggcaagtaa ctcgattaaa gaggagaaaa tataatgacg gcag                   44

<210> SEQ ID NO 12
<211> LENGTH: 41
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 12
gcccttgggg ctcgagttat ttgatgaaac cgctcagatg g                           41

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5
```

MICROORGANISMS AND PROCESSES FOR THE PRODUCTION OF ISOPRENE

RELATED APPLICATIONS

This application claims the benefit of U.S. Provisional Application No. 61/776,485, filed on Mar. 11, 2013 and U.S. Provisional Application No. 61/688,514, filed on May 16, 2012. The entire teachings of the above applications are incorporated herein by reference.

FIELD OF THE INVENTION

The present disclosure generally relates to the use of a non-naturally occurring microorganism for the production of isoprene. More specifically, the present disclosure relates to non-naturally occurring microorganisms that have been modified to express enzymes that enable the production of isoprene from different alcohols, in particular 3-methyl-2-buten-1-ol or 2-methyl-3-buten-2-ol.

BACKGROUND OF THE INVENTION

Currently, many high-value chemicals or fuels are typically manufactured by thermochemical processes from hydrocarbons, including petroleum oil and natural gas. Also, high value chemicals may be produced as "by-products" during the processing of crude oil into usable fractions. For example, isoprene has typically been produced during the catalytic cracking of crude oil fractions. However, recently catalytic cracker users have shifted their focus from crude oil to natural gas, resulting in a reduced source of the four and five carbon chain molecules that are found in crude oil, but not natural gas.

Being a short-chain carbon molecule, isoprene is a useful starting material for synthesizing a variety of chemicals. Isoprene may be used as a monomer or co-monomer for the production of higher value polymers. Examples of chemicals that can be produced using isoprene include polyisoprene, polybutylene, styrene-isoprene-styrene block co-polymers, and others. An example of an industry that uses isoprene is the synthetic rubber industry.

Given the increasing demand, decreasing supply and the many uses of isoprene, a new method of isoprene production is desired. Also, as the concerns of energy security, increasing oil and natural gas prices, and global warming escalate, the chemical production industry is seeking ways to replace chemicals made from non-renewable feedstocks with chemicals produced from renewable feedstocks using environmentally friendly practices.

The biological production of isoprene has been studied since the 1950s (Sharkey, T. D. 2009. The Future of Isoprene Research. Bull. Georg. Natl. Acad. Sci. 3: 106-113). Although many different organisms are known to emit isoprene, so far the biochemical pathway for isoprene production has only been elucidated in a few plant species. In plants, it appears that isoprene is produced in the chloroplast or other plastids from dimethylallyl diphosphate, also referred to herein as dimethylallyl pyrophosphate (DMAPP), in a single step by isoprene synthase, a nuclearly encoded enzyme that is routed to the plastid by a plastid targeting signal sequence. The isoprene synthases generally have a high Michaelis-Menten constant ($K_m$), typically 1 millimolar or higher, and thus require high concentrations of dimethylallyl diphosphate to function efficiently.

Although microbes that naturally produce isoprene are known in the art (Kuzma, J., Nemecek-Marshall, M., Pollock, W. H., and R. Fall. 1995. Bacteria produce the volatile hydrocarbon isoprene. Curr. Microbiol. 30: 97-103; Wagner, W. P., Nemecek-Marshall, M., and R. Fall. 1999. Three distinct phases of isoprene formation during growth and sporulation of *Bacillus subtilis*. J. Bact. 181: 4700-4703; Fall, R. and S. D. Copley. 2000. Bacterial sources and sinks of isoprene, a reactive atmospheric hydrocarbon. Env. Microbiol. 2: 123-130; Xue, J., and B. K. Ahring. 2011. Enhancing isoprene production by the genetic modification of the 1-deoxy-D-xylulose-5-phosphate pathway in *Bacillus subtilis*. Appl. Env. Microbiol. 77: 2399-2405), the mechanism of isoprene production is unknown and the levels of isoprene production are relatively low. Several non-naturally occurring microorganisms have been engineered to produce isoprene, e.g., U.S. patent application Ser. No. 12/335,071, wherein isoprene production requires an isoprene synthase. For efficient function of isoprene synthase, high intracellular levels of dimethylallyl diphosphate are required; however, high levels of intracellular dimethylallyl diphosphate are also toxic to the cells, retarding growth and reducing the rates and yields of isoprene production (Martin, V. J. J., Pitera, D. J., Withers, S. T., Newman, J. D. and J. D. Keasling. 2003. Engineering a mevalonate pathway in *Escherichia coli* for production of terpenoids. Nature Biotech. 21: 796-802; Withers, S. T., Gottlieb, S. S., Lieu, B., Newman, J. D., and J. D. Keasling. 2007. Identification of isopentenol biosynthetic genes from *Bacillus subtilis* by a screening method based on isoprenoid precursor toxicity. Appl. Env. Microbiol. 73: 6277-7283; Sivy, T. L., Fall, R., and T. N. Rosentiel. 2011. Evidence of isoprenoid precursor toxicity in *Bacillus subtilis*. Biosci. Biotechnol. Biochem. 75: 2376-2383). The problems associated with the direct chemical conversion of DMAPP to isoprene by isoprene synthases limits the potential for the biological production of commercially relevant amounts of isoprene.

Thus, there is a need for microorganisms and processes for the more efficient biological production of isoprene.

SUMMARY OF THE INVENTION

Embodiments of the present invention generally provide enzymes, non-naturally occurring microorganisms, and methods of producing isoprene.

Embodiments of the invention provide non-naturally occurring microbial organisms, i.e., microorganisms that include a biosynthetic isoprene pathway. The microorganisms include an exogenous nucleic acid encoding an enzyme of the biosynthetic pathway. The enzyme is a 2-methyl-3-buten-2-ol dehydratase, and the biosynthetic pathway is expressed at a sufficient level to produce isoprene. The biosynthetic pathway may further comprise a 2-methyl-3-buten-2-ol isomerase. The 2-methyl-3-buten-2-ol isomerase may be part of a bi-functional enzyme that also has the 2-methyl-3-buten-2-ol dehydratase activity. An example of such a bi-functional enzyme is a linalool dehydratase-isomerase. The microorganism may further comprise a 3-methyl-2-buten-1-ol synthase.

In another embodiment, a non-naturally occurring microorganism comprising a biosynthetic isoprene pathway is provided, wherein the microorganism comprises an exogenous nucleic acid encoding an enzyme of the biosynthetic isoprene pathway, 2-methyl-3-buten-2-ol dehydratase. The pathway further comprises a 2-methyl-3-buten-2-ol synthase, and the pathway is expressed at a sufficient level to produce isoprene.

In one embodiment, the present invention provides for a non-naturally occurring microorganism comprising at least one or more exogenous nucleic acids encoding one or more enzymes of an isoprene biosynthetic pathway, wherein the one or more enzymes of an isoprene biosynthetic pathway are expressed in sufficient amounts to produce isoprene, said isoprene biosynthetic pathway comprising a 3-methyl-2-buten-1-ol synthase, a 2-methyl-3-buten-2-ol isomerase, and a 2-methyl-3-buten-2-ol dehydratase.

In another embodiment, the present invention provides for a non-naturally occurring microorganism comprising at least one or more exogenous nucleic acids encoding one or more enzymes of an isoprene biosynthetic pathway, wherein the one or more enzymes of an isoprene biosynthetic pathway are expressed in sufficient amounts to produce isoprene, said isoprene biosynthetic pathway comprising a 2-methyl-3-buten-2-ol synthase and a 2-methyl-3-buten-2-ol dehydratase.

In an additional embodiment, the present invention provides for a method of producing isoprene, the method comprising the steps of culturing a non-naturally occurring microbial organism comprising at least one or more exogenous nucleic acids encoding one or more enzymes of an isoprene biosynthetic pathway, wherein the one or more enzymes of an isoprene biosynthetic pathway are expressed in sufficient amounts to produce isoprene, in a suitable culture medium containing a carbon source under conditions such that the non-naturally occurring microorganism converts at least a part of the carbon source to isoprene, and recovering the isoprene.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3 shows an *E. coli*-codon-optimized nucleic acid sequence (SEQ ID NO: 1), including an artificial ribosome binding site and an amino-terminal 6-histidine epitope tag, for the linalool dehydratase isomerase of *Castellaniella defragrans* strain 65Phen.

FIG. 4 shows an *E. coli*-codon-optimized nucleic acid sequence (SEQ ID NO: 2), including an artificial ribosome binding site and an amino-terminal 6-histidine epitope tag, for strawberry alcohol acyltransferase.

FIG. 11 shows an *E. coli*-codon-optimized nucleic acid sequence (SEQ ID NO: 3), including an artificial ribosome binding site, for the *Bacillus subtilis* yhfR gene.

FIG. 12 shows an *E. coli*-codon-optimized nucleotide sequence (SEQ ID NO: 4), including artificial binding sites and restriction endonuclease sites for subcloning, for a synthetic operon encoding FaNES1 from strawberry and idi from *H. pluvialis*.

FIG. 21 shows the DNA sequence (SEQ ID NO: 5) of plasmid pGA31R-mcs.

FIG. 22 shows the DNA sequence (SEQ ID NO: 6) of plasmid pGS31R-mcs.

FIG. 23 shows the *E. coli*-codon-optimized sequence (SEQ ID NO: 7) of the mvaE and mvaS genes of *Enterococcus faecalis* ATCC 700802, including incorporated ribosome binding sites and flanking restriction endonuclease sites used in subsequent cloning steps.

FIG. 24 shows the *E. coli*-codon-optimized sequence (SEQ ID NO: 8) of the synthetic operon encoding the mevalonate kinase gene of *Methanocaldococcus jannaschi*, the phosphomevalonate kinase gene of *Enterococcus faecalis* ATCC 700802, the mevalonate diphosphate decarboxylase gene of *Saccharomyces cerevisiae* S288C, and the isopentenyl diphosphate isomerase gene of *E. coli* MG1655, including incorporated ribosome binding sites and flanking restriction endonuclease sites used in subsequent cloning steps.

DETAILED DESCRIPTION

Figure 1:
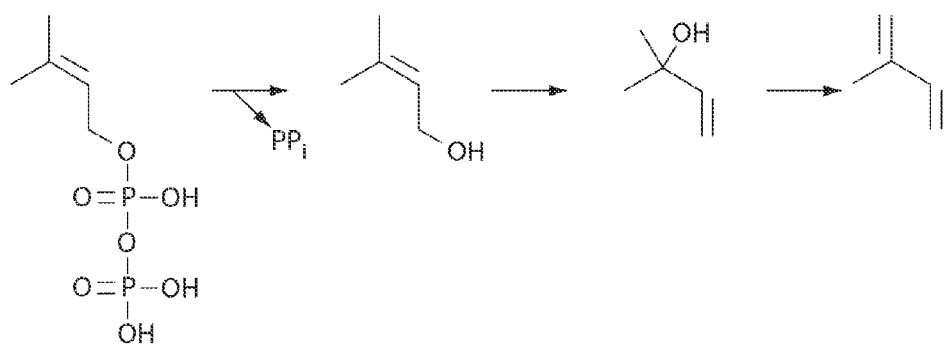
FIG. 1 shows an isoprene biosynthetic pathway comprising a 3-methyl-2-buten-1-ol synthase, a 2-methyl-3-buten-2-ol isomerase, and a 2-methyl-3-buten-2-ol dehydratase.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a glycerol dissimilation or isoprene biosynthetic pathway. As defined herein, an "isoprene biosynthetic pathway" comprises a pathway, e.g., a series of one or more enzymes or activities involved in the production of isoprene by an organism, i.e., biologically, wherein one or more of those enzymes or activities is exogenous to the organism.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbe," "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbial organisms of the invention can contain stable genetic alterations, which refer to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *Escherichia coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or non-orthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if the proteins that they code for share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by structure or ancestry but with different functions. These might arise by, for example, duplication of a gene followed by evolutionary divergence to produce proteins with similar or common, but not identical functions. Paralogs can originate or derive from the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A non-orthologous gene displacement is a non-orthologous gene from one species that can substitute for a referenced gene function in a different species. Substitution includes, for example, being able to perform substantially the same or a similar function in the species of origin compared to the referenced function in the different species. Although generally, a non-orthologous gene displacement will be identifiable as structurally related to a known gene encoding the referenced function, less structurally related but functionally similar genes and their corresponding gene products nevertheless will still fall within the meaning of the term as it is used herein. Functional similarity requires at least some structural similarity in the active site or binding region of a non-orthologous gene product compared to a gene encoding the function sought to be substituted. Therefore, examples of non-orthologous genes include paralogs or unrelated genes.

Therefore, in identifying and constructing the non-naturally occurring microbial organisms of the invention having an isoprene biosynthetic pathway, those skilled in the art will understand with applying the teaching and guidance provided herein to a particular species that the identification of metabolic modifications can include identification and inclusion or inactivation of orthologs. To the extent that paralogs and/or non-orthologous gene displacements are present in the referenced microorganism that encode an enzyme catalyzing a similar or substantially similar metabolic reaction, those skilled in the art also can utilize these evolutionarily related genes. Orthologs, paralogs and non-orthologous gene displacements can be determined by methods well known to those skilled in the art. As defined herein, enzymes or genes that are described or claimed as being "derived from" an organism include any homologs, paralogs, non-orthologous gene displacements that have substantially similar activity.

The methods and techniques utilized for culturing or generating the microorganisms disclosed herein are known to the skilled worker trained in microbiological and recombinant DNA techniques. Methods and techniques for growing microorganisms (e.g., bacterial cells), transporting isolated DNA molecules into the host cell and isolating, cloning and sequencing isolated nucleic acid molecules, knocking out expression of specific genes, etc., are examples of such techniques and methods. These methods are described in many items of the standard literature, which are incorporated herein in their entirety: "Basic Methods In Molecular Biology" (Davis, et al., eds. McGraw-Hill Professional, Columbus, Ohio, 1986); Miller, "Experiments in Molecular Genetics" (Cold Spring Harbor Laboratory Press, Cold Spring Harbor, N.Y., 1972); Miller, "A Short Course in Bacterial Genetics" (Cold Spring Harbor Laboratory Press, Cold Spring Harbor, N.Y., 1992); Singer and Berg, "Genes and Genomes" (University Science Books, Mill Valley, Calif., 1991); "Molecular Cloning: A Laboratory Manual," $2^{nd}$ Ed. (Sambrook, et al., eds., Cold Spring Harbor Laboratory Press, Cold Spring Harbor, N.Y., 1989); "Handbook of Molecular and Cellular Methods in Biology and Medicine" (Kaufman, et al., eds., CRC Press, Boca Raton, Fla., 1995); "Methods in Plant Molecular Biology and Biotechnology" (Glick and Thompson, eds., CRC Press, Boca Raton, Fla., 1993); and Smith-Keary, "Molecular Genetics of *Escherichia coli*" (The Guilford Press, New York, N.Y., 1989).

Although the direct conversion of dimethylallyl diphosphate to isoprene by isoprene synthase enzymes is known in the art, we have shown that isoprene can also be produced from two different alcohols, 3-methyl-2-buten-1-ol and 2-methyl-3-buten-2-ol, using linalool dehydratase-isomerase (see Example 1 and Example 2 and FIGS. 6 and 8), an enzyme isolated from *Castellaniella defragrans* strain 65Phen. The linalool dehydratase isomerase permits the development of novel isoprene biosynthetic pathways of either two or three steps. In a two-step isoprene biosynthetic pathway, dimethylallyl diphosphate is converted to 2-methyl-3-buten-2-ol by an enzyme such as a 2-methyl-3-buten-2-ol synthase, followed by conversion of 2-methyl-3-buten-2-ol to isoprene. In a three-step isoprene biosynthetic pathway, dimethylallyl diphosphate is converted to 3-methyl-2-buten-1-ol by either a phosphatase or a terpene synthase capable of converting dimethylallyl diphosphate to 3-methyl-2-buten-1-ol, 3-methyl-2-buten-1-ol is converted to 2-methyl-3-buten-2-ol by a 2-methyl-3-buten-2-ol isomerase, and 2-methyl-3-buten-2-ol is converted to isoprene by a 2-methyl-3-buten-2-ol dehydratase. As demonstrated in Example 1 and Example 2, the *Castellaniella defragrans* linalool dehydratase-isomerase functions as both a 2-methyl-3-buten-2-ol isomerase and a 2-methyl-3-buten-2-ol dehydratase.

Both the three-step isoprene biosynthetic pathway and the two-step isoprene biosynthetic pathway are expressed at a sufficient level to produce isoprene in detectable quantities. The isoprene may be detected and characterized by gas chromatography/mass spectrometry, for example.

Three-Step Isoprene Biosynthetic Pathway

As used herein, enzyme names are defined as follows. A 2-methyl-3-buten-2-ol dehydratase is an enzyme that catalyzes the conversion of 2-methyl-3-buten-2-ol to isoprene. A 2-methyl-3-buten-2-ol synthase is an enzyme that catalyzes the conversion of dimethylallyl diphosphate to 2-methyl-3-buten-2-ol. A 3-methyl-2-buten-1-ol synthase or prenol synthase is an enzyme that catalyzes the conversion of dimethylallyl diphosphate to 3-methyl-2-buten-1-ol also referred to herein as prenol. A 2-methyl-3-buten-2-ol isomerase is an enzyme that catalyzes the isomerization of 3-methyl-2-buten-1-ol to 2-methyl-3-buten-2-ol.

In one embodiment of the present invention, a non-naturally occurring microorganism containing one or more exogenous genes encoding enzymes of an isoprene biosynthetic pathway convert dimethylallyl diphosphate to isoprene in three steps (as used herein, "three-step isoprene biosynthetic pathway," FIG. 1). In a first step, dimethylallyl diphosphate is converted to 3-methyl-2-buten-1-ol by a 3-methyl-2-buten-1-ol synthase. In a second step, 3-methyl-2-buten-1-ol is converted to 2-methyl-3-buten-2-ol by a 2-methyl-3-buten-2-ol isomerase. In a third step, 2-methyl-3-buten-2-ol is converted to isoprene by a 2-methyl-3-buten-2-ol dehydratase.

In a preferred embodiment of a naturally occurring microorganism for the conversion of dimethylallyl diphosphate to isoprene in three steps, the first step is catalyzed by a 3-methyl-2-buten-1-ol synthase and the second and third steps are catalyzed by a single, bi-functional enzyme with both 2-methyl-3-buten-2-ol isomerase and 2-methyl-3-buten-2-ol dehydratase activities.

The conversion of dimethylallyl diphosphate to 3-methyl-2-buten-1-ol (prenol) may be catalyzed by a phosphatase. Examples of such phosphatases include enzymes encoded by the *Bacillus subtilis* genes yqkG (nudF) and yhfR (Withers, S. T., Gottlieb, S. S., Lieu, B., Newman, J. D. and J. D. Keasling. 2007. Identification of isopentenol biosynthetic genes from *Bacillus subtilis* by a screening method based on isoprenoid precursor toxicity. Appl. Env. Microbiol. 73: 6277-6283), although other known phosphatases and coding sequences with predicted phosphatase activity, for example the ytjC gene of *E. coli*, may be used. Table 1, below, provides examples of phosphatases for use in the conversion of dimethylallyl diphosphate to prenol.

TABLE 1

| Locus | GenBank Accession No. | Organism |
|---|---|---|
| BAA12639 (YqkG) | BAA12639 | *Bacillus subtilis* |
| CAA74541 (YhfR) | CAA74541 | *Bacillus subtilis* subsp. *subtilis* Strain 168 |
| GPMB_ECOLI | P0A7A2 | *Escherichia coli* K-12 Calf Intestine Alkaline Phosphatase Shrimp Alkaline Phosphatase. |

The conversion of dimethylallyl diphosphate to 3-methyl-2-buten-1-ol may be catalyzed by a terpene synthase, e.g., a geraniol synthase or farnesol synthase or mutants thereof, for example. Table 2, below, provides examples of terpene synthases for use in the conversion of dimethylallyl diphosphate to 3-methyl-2-buten-1-ol.

TABLE 2

| Locus | GenBank Accession No. | Organism |
|---|---|---|
| Geraniol Synthase | | |
| AAR11765 | AAR11765 | *Ocimum basilicum* |
| ABB30216 | ABB30216 | *Perilla citriodora* |
| ABB30217 | ABB30217 | *Perilla citriodora* |
| ABB30218 | ABB30218 | *Perilla frutescens* |
| CAE52821 | CAE52821 | *Cinnamomum tenuipile* |
| Farnesol Synthase | | |
| ACSS_MAIZE | Q84ZW8 | *Zea mays* |
| ABJ16554 | ABJ16554 | *Oryza sativa*. |

3-methyl-2-buten-1-ol is isomerized to 2-methyl-3-buten-2-ol by a 2-methyl-3-buten-2-ol isomerase. As used herein, a 2-methyl-3-buten-2-ol isomerase is an enzyme that converts 3-methyl-2-buten-1-ol (prenol) to 2-methyl-3-buten-2-ol in a reversible reaction. An example of such an enzyme is the linalool dehydratase-isomerase of *Castellaniella defragrans* strain 65Phen, GenBank accession number FR669447. This enzyme catalyzes the isomerization of 3-methyl-2-buten-1-ol to 2-methyl-3-buten-2-ol and the dehydration of 2-methyl-3-buten-2-ol to isoprene (Example 1, below, and FIG. 6). Orthologs, paralogs and non-orthologous gene displacements of linalool dehydratase-isomerase can be determined by methods well known to those skilled in the art.

As used herein, a 2-methyl-3-buten-2-ol dehydratase is an enzyme that converts 2-methyl-3-buten-2-ol to isoprene. An example of such an enzyme is the linalool dehydratase-isomerase of *Castellaniella defragrans* strain 65Phen, GenBank accession number FR669447. This enzyme is capable of catalyzing the dehydration of 2-methyl-3-buten-2-ol to isoprene (Example 2, below, and FIG. 8). Orthologs, paralogs and non-orthologous gene displacements of linalool dehydratase-isomerase can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence that can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity that is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

2-methyl-3-buten-2-ol dehydratase enzyme activity has also been identified in *Aquincola tertiaricarbonis* (Schuster, J., Schäfer, F., Hübler, N., Brandt, A., Rosell, M., Härtig, C., Harms, h., Müller, R. H. and T. Rohwerder. 2012. Bacterial degradation of tert-amyl alcohol proceeds via hemiterpene 2-methyl-3-buten-2-ol by employing the tertiary alcohol desaturase function of the Rieske nonheme mononuclear iron oxygenase MdpJ. J. Bact. 194: 972-981). The sequence of this 2-methyl-3-buten-2-ol dehydratase has not been reported.

Two-Step Isoprene Biosynthetic Pathway

Figure 2:
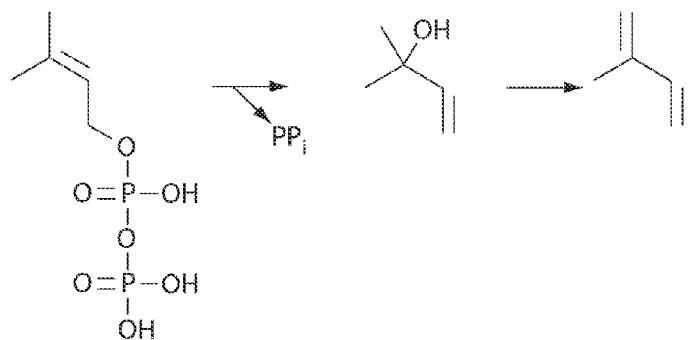
FIG. 2 shows an isoprene biosynthetic pathway comprising a 2-methyl-3-buten-2-ol synthase and a 2-methyl-3-buten-2-ol dehydratase.

In another embodiment, a non-naturally occurring microorganism containing one or more exogenous genes encoding enzymes of an isoprene biosynthetic pathway convert dimethylallyl diphosphate to isoprene in two steps catalyzed by a 2-methyl-3-buten-2-ol synthase (MBO synthase) and a 2-methyl-3-buten-2-ol dehydratase (as used herein, "two-step isoprene biosynthetic pathway," FIG. 2).

As used herein, an example of a 2-methyl-3-buten-2-ol synthase is a naturally occurring polypeptide found in some plant plastids, particularly in the chloroplast, that converts dimethylallyl diphosphate to 2-methyl-3-buten-2-ol, and derivatives (mutants) of polypeptides that naturally convert dimethylallyl diphosphate to 2-methyl-3-buten-2-ol. MBO synthases are characterized, in part, by an amino-terminal plastid targeting sequence that routes the polypeptide to the chloroplast. Upon translocation into the chloroplast, the transit peptide may be cleaved from the polypeptide to yield a mature protein that is smaller in molecular weight than the precursor protein. For overexpression of an exogenous MBO synthase in a microbial organism, it is preferable to express a truncated MBO synthase that approximates the mature form found in nature, rather than the precursor form. Essentially, the sequence encoding the transit peptide is removed from the MBO synthase coding sequence. While visual inspection may allow one skilled in the art to select where to truncate the isoprene synthase coding sequence, computer-based algorithms such as ChloroP 1.1 can be used to help predict which amino acids belong to the transit peptide (Emanuelsson, O., Nielsen, H., G. von Heijne. 1999. ChloroP, a neural network-based method for predicting chloroplast transit peptides and their cleavage sites. Protein Sci. 8: 978-984). An example of an MBO synthase is found in *Pinus sabiniana*, with the GenBank accession number AEB53064.1.

The conversion of dimethylallyl diphosphate to 2-methyl-3-buten-2-ol may be catalyzed by a terpene synthase, e.g., a linalool synthase (e.g. E.C. No. 4.2.3.25 or 4.2.3.26) or nerolidol synthase or mutants thereof, for example. Table 3, below, provides examples of terpene synthases for use in the conversion of dimethylallyl diphosphate to 2-methyl-3-buten-2-ol.

TABLE 3

| Locus | GenBank Accession No. | Organism |
|---|---|---|
| S-Linalool Synthase | | |
| LIS_CLABR | Q96376 | *Clarkia breweri* |
| LINS_ARATH | Q84UV0 | *Arabidopsis thaliana* |
| C0KWV3_9LAMI | C0KWV3 | *Perilla setoyensis* |
| C0KWV5_PERFR | C0KWV5 | *Perilla frutescens* var. *hirtella* |
| C0KWV7_PERFR | C0KWV7 | *Perilla frutescens* var. *hirtella* |
| D4N3A0_9ERIC | D4N3A0 | *Actinidia arguta* |
| D4N3A1_9ERIC | D4N3A1 | *Actinidia polygama* |
| R-Linalool Synthase | | |
| LLOS1_ARTAN | Q9SPN0 | *Artemesia annua* |
| LLOS_OCIBA | Q5SBP3 | *Ocimum basilicum* |
| LLOS5_ARTAN | Q9SPN1 | *Artemesia annua* |
| LLOS_MENAQ | Q8H2B4 | *Mentha aquatica* |
| Q1XBU5_SOLLC | Q1XBU5 | *Solanum lycopersicum* |
| (3S,6E)-Nerolidol Synthase | | |
| Q5UB06_MEDTR | Q5UB06 | *Medicago trunculata* |
| F8TWD1_POPTR | F8TWD1 | *Populus trichocarpa* |
| NES1_FRAVE | P0CV96 | *Fragaria vesca* |
| NES1_FRAAN | P0CV94 | *Fragaria ananassa* |
| NES2_FRAAN | P0CV95 | *Fragaria ananassa.* |

One example of the use of a terpene synthase to convert dimethylallyl diphosphate to 2-methyl-3-buten-2-ol is found in Example 3.

The conversion of 2-methyl-3-buten-2-ol to isoprene may be catalyzed by a 2-methyl-3-buten-2-ol dehydratase as described above. The 2-methyl-3-buten-2-ol dehydratase may be a bi-functional enzyme with both 2-methyl-3-buten-2-ol isomerase and 2-methyl-3-buten-2-ol dehydratase activities, such as the linalool dehydratase-isomerase described above, or the enzyme may encode only the 2-methyl-3-buten-2-ol dehydratase activity without a 2-methyl-3-buten-2-ol isomerase activity.

In a preferred embodiment of the present invention, dimethylallyl diphosphate available for conversion to isoprene by either a two-step isoprene biosynthetic pathway or a three-step isoprene biosynthetic pathway may be increased by overexpression of one or more endogenous genes or expression of one or more exogenous genes encoding enzymes of the methylerythritol phosphate pathway: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, 1-hydroxy-2-methyl-2-(E)-butenyl-4-diphosphate synthase, dimethylallyl-diphosphate/isopentenyl-diphosphate:NAD(P)$^+$ oxidoreductase, or isopentenyl diphosphate isomerase. For example, expression of exogenous genes encoding 1-deoxy-D-xylulose-5-phosphate synthase, 1-deoxy-D-xylulose-5-phosphate reductoisomerase, and isopentenyl diphosphate isomerase may result in increased levels of dimethylallyl diphosphate, and when expressed in conjunction with either a two-step isoprene biosynthetic pathway or a three-step isoprene biosynthetic pathway, result in increased yields of isoprene.

In another preferred embodiment of the present invention, dimethylallyl diphosphate available for conversion to isoprene by either a two-step isoprene biosynthetic pathway or a three-step isoprene biosynthetic pathway may be increased by expression of one or more exogenous genes encoding enzymes of the mevalonate pathway including, but not limited to: acetyl-CoA acetyltransferase (also known as thiolase), 3-hydroxy-3-methylglutaryl-CoA synthase, 3-hydroxy-3-methylglutaryl-CoA reductase, mevalonate kinase, phosphomevalonate kinase, diphosphomevalonate decarboxylase, and isopentenyl diphosphate isomerase. One example of overexpression of exogenous genes encoding the mevalonate pathway is described in Example 4.

In an additional embodiment, the present invention provides for a method of producing isoprene, the method comprising the steps of culturing a non-naturally occurring microbial organism comprising at least one or more exogenous nucleic acids encoding one or more enzymes of an isoprene biosynthetic pathway, wherein the one or more enzymes of an isoprene biosynthetic pathway are expressed in sufficient amounts to produce isoprene, in a suitable culture medium containing a carbon source under conditions such that the non-naturally occurring microorganism converts at least a part of the carbon source to isoprene, and recovering the isoprene. The carbon source may be or comprise glycerol, glucose, xylose, arabinose, or mixtures thereof; dimethylallyl diphosphate, 3-methyl-2-buten-1-ol, or 2-methyl-3-buten-2-ol. Preferably, the carbon source is or comprises glycerol, glucose or sugars derived from cellulosic biomass processes. The isoprene may be recovered as described in the examples below.

In the following examples of embodiments of the current invention, the common *E. coli* strain BL21 was used for the examples. BL21 (Life Technologies, Inc., Carlsbad, Calif.) cells were made electrocompetent and electroporated following the protocol from the MicroPulser Electroporation Apparatus Operating Instructions and Applications Guide (Bio-Rad catalog number 165-2100), except that LB without salt was used to grow up the culture in making cells electrocompetent.

EXAMPLE 1

Microorganism for the Production of Isoprene from 3-Methyl-2-Buten-1-Ol

This working example shows the production of isoprene from 3-methyl-2-buten-1-ol by a non-naturally occurring microorganism expressing one or more exogenous genes of an isoprene biosynthetic pathway.

The plasmid pJ404-LDI was constructed by DNA2.0 (Menlo Park, Calif.) using the *E. coli*-codon-optimized sequence (SEQ ID NO: 1) of the linalool dehydratase-isomerase (LDI) of *Castellaniella defragrans* strain 65Phen. The LDI coding sequence was codon-optimized for expression in *E. coli*, synthesized and inserted into the plasmid expression vector pJexpress404. The resulting plasmid, pJ404-LDI, was electroporated into *E. coli* BL21 electrocompetent cells.

Plasmid pJ404-SAAT was constructed by DNA2.0 (Menlo Park, Calif.) using the codon-optimized sequence (SEQ ID NO: 2) of the strawberry acyl-CoA transferase (SAAT). The SAAT coding sequence was codon-optimized for expression in *E. coli*, synthesized and inserted into the plasmid expression vector pJexpress404. The resulting plasmid, pJ404-SAAT, was electroporated into *E. coli* BL21 electrocompetent cells. pJ404-SAAT was used as a negative control.

Transformants of BL21 harboring either pJ404-LDI or pJ404-SAAT were selected on Luria-Bertani (LB)-agar plates (10 g/L yeast extract, 5 g/L Bacto Tryptone, 10 g/L sodium chloride, 15 g/L Bacto Agar) containing 100 µg/ml ampicillin.

A single colony of BL21 harboring pJ404-LDI or pJ404-SAAT from the LB-agar plates was used to inoculate 10 ml of LB broth (10 g/L yeast extract, 5 g/L Bacto Tryptone, 10 g/L sodium chloride) containing 100 µg/ml ampicillin contained in 125-mL Erlenmeyer flasks. Flasks were incubated for 16 hours at 37° C. in a rotary shaking incubator. After 16 hours, the resulting cultures were diluted using fresh LB broth containing 100 µg/ml ampicillin to an optical density of 0.16 at 600 nm. 50 ml of the diluted cultures were placed in 300-ml Erlenmeyer flasks and incubated at 37° C. in a rotary shaking incubator until the optical density at 600 nm reached approximately 0.6, typically 90 minutes. 4 ml of the resulting cultures were then placed into 20 ml gas chromatography headspace vials. 3-methyl-2-buten-1-ol was added to a final concentration of 1 mM, IPTG (Isopropyl β-D-1-thiogalactopyranoside) was added to 0.1 mM, and the cultures were grown for an additional 16 hours at 37° C. with shaking.

Isoprene was measured using headspace analysis on an Agilent 7890A GC equipped with a CTC-PAL autosampler and a FID. Headspace vials (20 ml) were incubated at 50° C. with agitation at 500 rpm for 2 minutes. Then 1 ml of the headspace was removed using a heated headspace syringe at 50° C. and injected into the GC inlet (250° C., split of 20:1). Samples were analyzed using a FID detector set at 300° C., with a helium carrier gas flow rate of 2 ml/min through a DB-624 30 m×530 µm×3 µm column (J&W Scientific), and an oven program of 85° C. for 5.25 minutes. The isoprene concentration in samples was calculated from calibration curves generated from isoprene calibration gas standards analyzed under the same GC/FID method. The isoprene product was also confirmed by headspace GC/MS using an Agilent 7890A GC equipped with a 5975C MSD and a CTC-PAL autosampler. Headspace vials were incubated at 85° C. with agitation at 600 rpm for 5 minutes. Then 1 ml of the headspace was removed using a heated headspace syringe at 85° C. and injected into the GC inlet (250° C., split of 25:1). The GC/MS method used helium as the carrier gas at 1 ml/min through a HP-5MS 30 m×250 µm×0.25 µm column (J&W Scientific), an oven program of 35° C. for 4 minutes, then ramped 25° C./min to 150° C., a MS source temperature of 230° C., and a quadrupole temperature of 150° C. The mass spectrometer was operated in scan mode from 25 to 160 mass units. The isoprene peak was identified by the NIST 11 MS Library, as well as comparison against an authentic sample (135 ppm isoprene, 135 ppm carbon dioxide in dry nitrogen gas, Matheson TRIGAS, Houston, Tex.).

3-methyl-2-buten-1-ol and 2-methyl-3-buten-2-ol were measured using headspace analysis on an Agilent 7890A GC equipped with a CTC-PAL autosampler and a FID. Headspace vials (20 ml) were incubated at 85° C. with agitation at 600 rpm for 5 minutes. Then 1 ml of the headspace was removed using a heated headspace syringe at 85° C. and injected into the GC inlet (250° C., split of 25:1). Samples were analyzed using a FID detector set at 350° C., with a helium carrier gas flow rate of 3 ml/min through at DB-624 30 m×530 µm×3 µm column (J&W Scientific), and an oven program of 90° C., then ramping 20° C./min to 230° C. for 3 minutes. The 3-methyl-2-buten-1-ol and 2-methyl-3-buten-2-ol concentrations in samples were calculated from calibration curves generated from diluted standards of each compound analyzed under the same GC/FID method.

Figure 5:
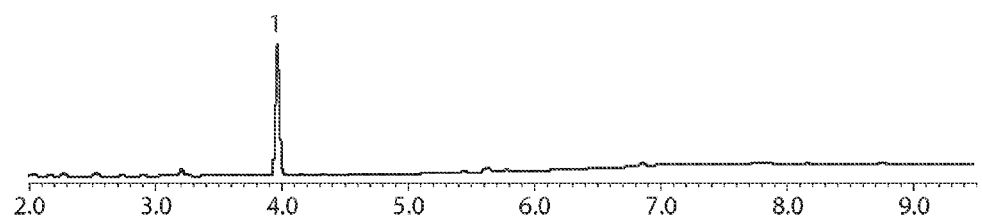
FIG. 5 shows a gas chromatogram of a 1 ml sample of the headspace of a 20-ml vial containing 1 mM 3-methyl-2-buten-1-ol dissolved in Luria Bertani broth. Peak 1 is 3-methyl-2-buten-1-ol, with a retention time of 3.96 minutes.
Figure 6:
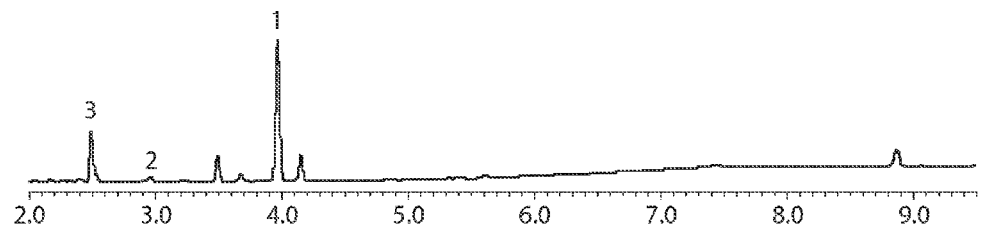
FIG. 6 shows a gas chromatogram of a 1 ml sample of the headspace of a 20 ml vial containing *E. coli* strain BL21 harboring plasmid pJ404-LDI cultured overnight on 1 mM 3-methyl-2-buten-1-ol in Luria Bertani broth supplemented with 100 µg/ml ampicillin. Peak 1 is 3-methyl-2-buten-1-ol, with a retention time of 3.96 minutes. Peak 2 is 2-methyl-3-buten-2-ol with a retention time of 2.96 minutes. Peak 3 is isoprene, with a retention time of 2.49 minutes.
Figure 9:
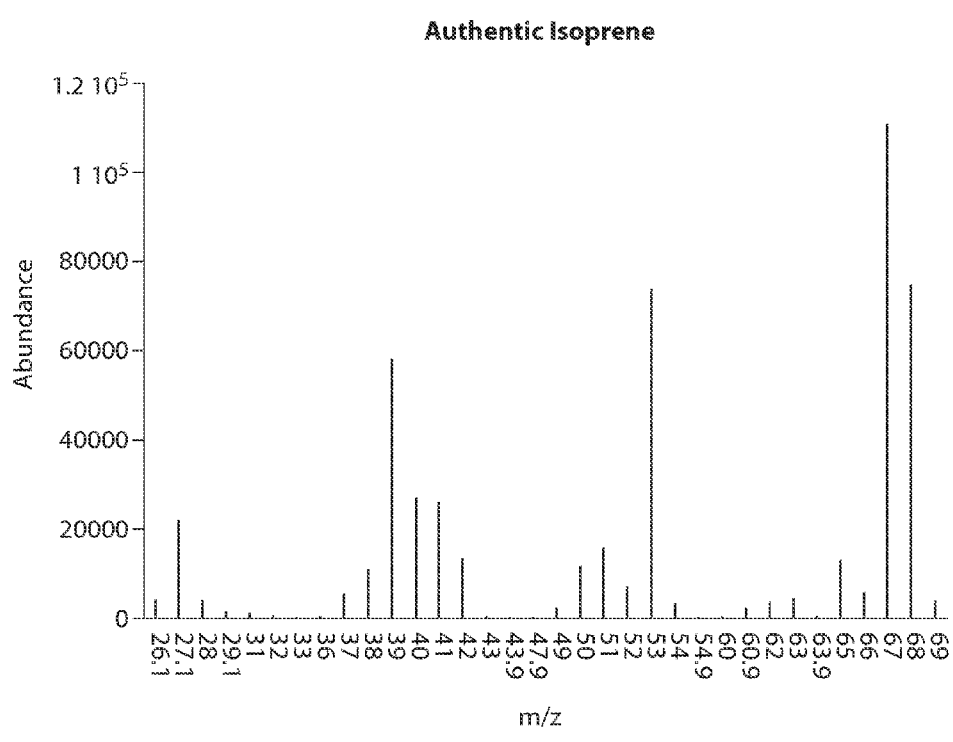
FIG. 9 shows the results of GC/MS analysis of authentic isoprene.
Figure 10:
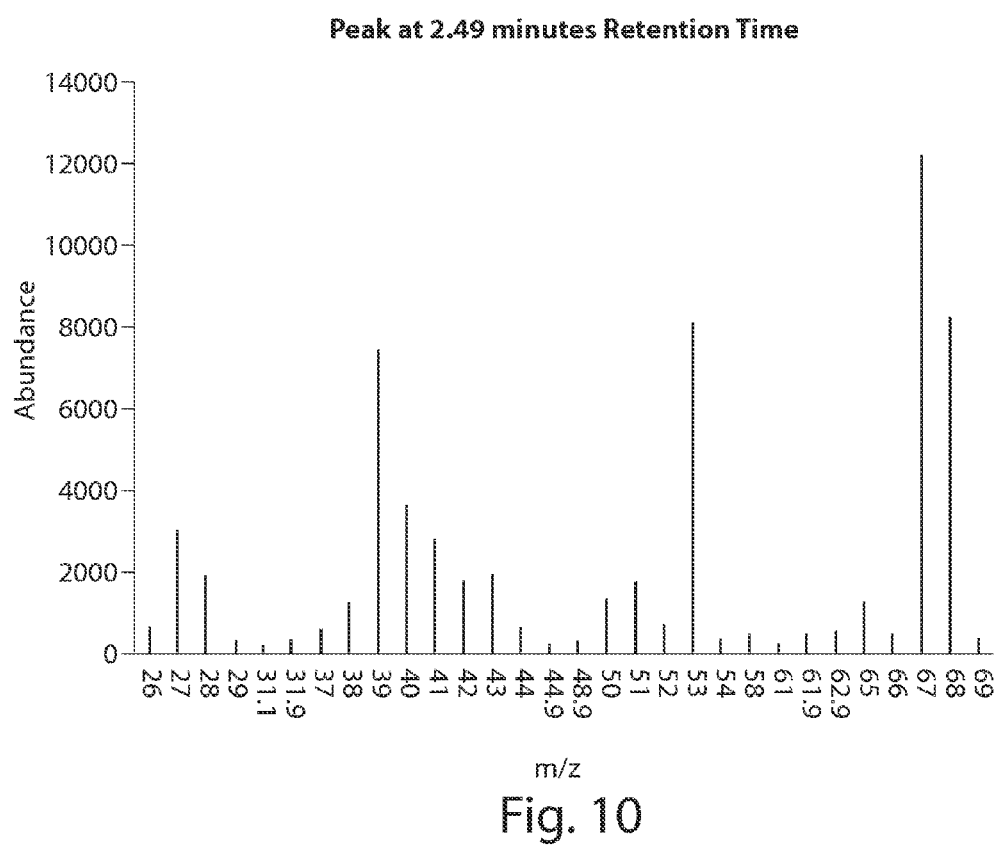
FIG. 10 shows the results of GC/MS analysis of the peak at 2.49 minutes from Example 1, verifying the identity of the peak as isoprene.

The results of this example are presented in FIG. 5 and FIG. 6. LB broth containing 1 mM 3-methyl-2-buten-1-ol without E. coli cells showed a peak at 3.96 minutes corresponding to 3-methyl-2-buten-1-ol (FIG. 5). Similarly, cultures containing 1 mM 3-methyl-2-buten-1-ol with BL21 cells harboring pJ404-SAAT showed a peak at 3.96 minutes corresponding to 3-methyl-2-buten-1-ol, and an additional peak corresponding to the aldehyde 3-methyl-2-buten-1-al (prenal, data not shown). In contrast, cultures containing 1 mM 3-methyl-2-buten-1-ol with BL21 cells harboring pJ404-LDI converted 3-methyl-2-buten-1-ol to 2-methyl-3-buten-2-ol and isoprene, corresponding to peaks at 2.96 minutes and 2.49 minutes, respectively. This demonstrates that E. coli cells harboring pJ404-LDI isomerize 3-methyl-2-buten-1-ol to 2-methyl-3-buten-2-ol and dehydrate 2-methyl-3-buten-2-ol to isoprene. FIG. 9 presents the GC/MS analysis of an authentic isoprene sample; FIG. 10 presents the GC/MS analysis of the peak with a 2.49 minute retention time, with the same fragmentation pattern as authentic isoprene shown in FIG. 9.

EXAMPLE 2

Microorganism for the Production of Isoprene from 2-Methyl-3-Buten-2-Ol

This working example shows the production of isoprene from 2-methyl-3-buten-2-ol by a non-naturally occurring microorganism expressing one or more exogenous genes of an isoprene biosynthetic pathway.

A single colony of BL21 harboring pJ404-LDI or pJ404-SAAT from LB-agar plates was used to inoculate 10 ml of LB broth (10 g/L yeast extract, 5 g/L Bacto Tryptone, 10 g/L sodium chloride) containing 100 µg/ml ampicillin contained in 125-mL Erlenmeyer flasks. Flasks were incubated for 16 hours at 37° C. in a rotary shaking incubator. After 16 hours, the cultures were diluted using fresh LB broth containing 100 µg/ml ampicillin to an optical density of 0.16 at 600 nm. 50 ml of the diluted cultures were placed in 300-mL Erlenmeyer flasks and incubated at 37° C. in a rotary shaking incubator until the optical density at 600 nm reached approximately 0.6, typically 90 minutes. 4 ml of the cultures were then placed into 20-ml gas chromatography headspace vials. 2-methyl-3-buten-2-ol was added to a final concentration of 1 mM. IPTG (Isopropyl β-D-1-thiogalactopyranoside) was added to a final concentration of 0.1 mM. Cultures containing 2-methyl-3-buten-2-ol were grown for 16 hours at 37° C. with shaking.

Isoprene, 3-methyl-2-buten-1-ol and 2-methyl-3-buten-2-ol were measured as above. The identity of the isoprene peak was also verified using GC/MS, as described above in Example 1.

Figure 7:
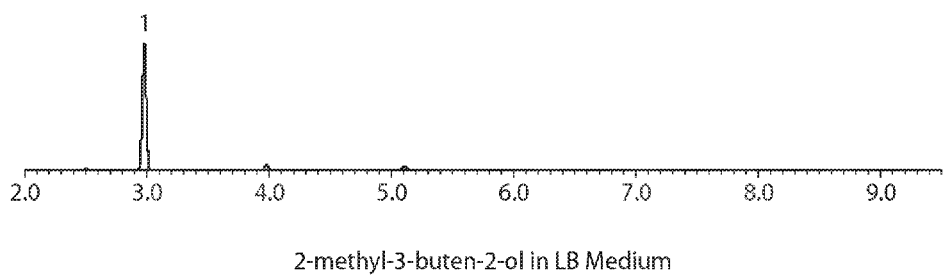
FIG. 7 shows a gas chromatogram of a 1 ml sample of the headspace of a 20 ml containing 1 mM 2-methyl-3-buten-2-ol dissolved in Luria Bertani broth. Peak 1 is 2-methyl-3-buten-2-ol with a retention time of 2.96 minutes.
Figure 8:
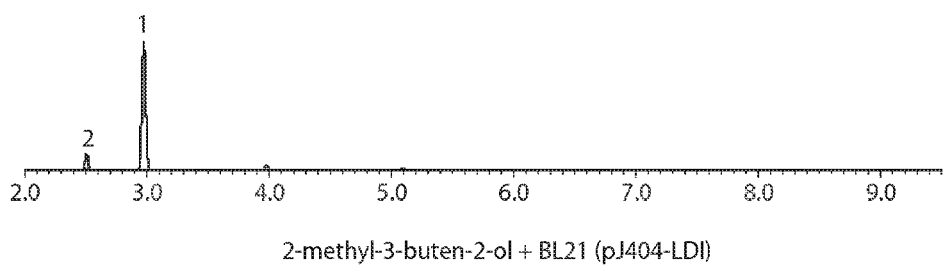
FIG. 8 shows a gas chromatogram of a 1 ml sample of the headspace of a 20-milliliter vial containing *E. coli* strain BL21 harboring plasmid pJ404-LDI cultured overnight on 1 mM 2-methyl-3-buten-2-ol in Luria Bertani broth supplemented with 100 µg/ml ampicillin. Peak 1 is 2-methyl-3-buten-2-ol with a retention time of 2.96 minutes. Peak 2 is isoprene with a retention time of 2.49 minutes.

The results of this example are presented in FIG. 7 and FIG. 8. LB broth containing 1 mM 2-methyl-3-buten-2-ol with E. coli cells omitted showed a peak at 2.96 minutes corresponding to 2-methyl-3-buten-2-ol (FIG. 7). Similarly, cultures containing 1 mM 2-methyl-3-buten-2-ol and BL21 cells harboring pJ404-SAAT showed a peak at 2.96 minutes corresponding to 2-methyl-3-buten-2-ol (data not shown). In contrast, cultures containing 1 mM 2-methyl-3-buten-2-ol and BL21 cells harboring pJ404-LDI converted 2-methyl-3-buten-2-ol to isoprene, corresponding to the peak at 2.49 minutes. This demonstrates that E. coli cells harboring pJ404-LDI dehydrate 2-methyl-3-buten-2-ol to isoprene.

EXAMPLE 3

FaNES1 Catalyzes Formation of 2-Methyl-3-Buten-2-Ol from Dimethylallyl Diphosphate This working example shows the production of 2-methyl-3-buten-2-ol from dimethylallyl diphosphate by a non-naturally occurring microorganism expressing an exogenous terpene synthase, the (3S,6E)-nerolidol synthase of *Fragaria ananassa*.

The plasmid pJ401-NES1-idi was constructed by DNA2.0 (Menlo Park, Calif.) using the codon-optimized sequence of the (3S,6E)-nerolidol synthase, FaNES1, of *Fragaria ananassa* (GenBank accession no. P0CV94; Aharoni, A., Giri, A. P., Verstappen, F. W. A., Bertea, C. M., Sevenier, R., Sun, Z., Jongsma, M. A., Schwab, W. and H. J. Bouwmeester. 2004. Gain and loss of fruit flavor compounds produced by wild and cultivated strawberry species. The Plant Cell 16: 3110-3131) and the codon-optimized isopentenyl diphosphate isomerase gene, idi, of *H. pluvialis*. Both the FaNES1 and idi coding sequences were codon-optimized for expression in E. coli, synthesized and inserted into the plasmid expression vector pJexpress401. The resulting plasmid, pJ401-NES1-idi, was electroporated into E. coli BL21 electrocompetent cells. The codon-optimized sequence (SEQ ID NO: 4), including artificial ribosomal binding sites and flanking restriction endonucleases for subcloning, is provided in FIG. 12.

The production of nerolidol, linalool and 2-methyl-3-buten-2-ol was assayed as follows. A single colony of BL21 harboring plasmid pJ401-NES1-idi from an LB-agar plate was used to inoculate 10 ml of LB broth (10 g/L yeast extract, 5 g/L Bacto Tryptone, 10 g/L sodium chloride) containing 50 µg/ml kanamycin. Flasks were incubated for 16 hours at 37° C. in a rotary shaking incubator. After 16 hours, the cultures were diluted using fresh LB broth containing 50 µg/ml kanamycin and 0.1 mM IPTG to yield an initial cell density at 600 nm of 0.4 to 0.5. 4 mL of the diluted culture was placed in a 20 ml GC vial and incubated for 6 or 24 hours at 30° C. with shaking. At 6 or 24 hours, the headspace gas was analyzed by GC/MS-SIM.

Figure 13:
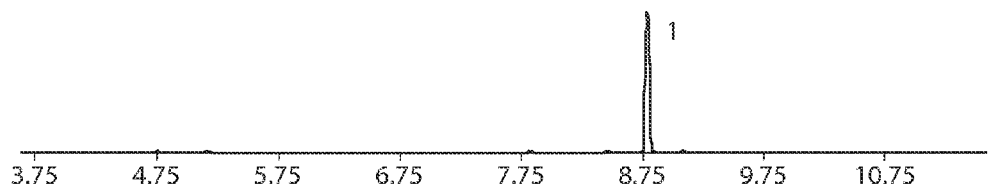
FIG. 13 shows a gas chromatogram of a 1 ml sample of the headspace of a 20 ml vial containing 1 mM linalool dissolved in Luria Bertani broth. Peak 1 is linalool, with a retention time of 8.8 minutes.
Figure 14:
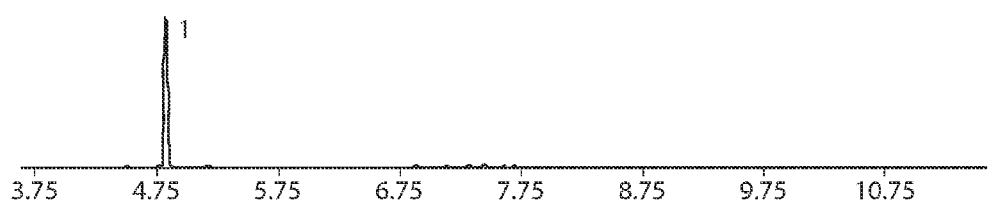
FIG. 14 shows a gas chromatogram of a 1 ml sample of the headspace of a 20 ml vial containing 1 mM 2-methyl-3-buten-2-ol dissolved in Luria Bertani broth under the same column conditions used to detect linalool. Peak 1 is 2-methyl-3-buten-2-ol, with a retention time of 4.8 minutes.

Samples were analyzed by headspace GC/MS in Select Ion Mode (SIM) using an Agilent 7890A GC equipped with a 5975C MSD and a CTC-PAL autosampler. Headspace vials (20 ml) were incubated at 85° C. with agitation at 600 rpm for 5 minutes. Then 1 ml of the headspace was removed using a heated headspace syringe at 85° C. and injected into the GC inlet (250° C., split of 25:1). Helium was used as the carrier gas at 1.5 ml/min through a VF-624MS 60 m×250 µm×1.4 µm column (J&W Scientific) and an oven program of 90° C. for 1 minute, then ramped 25° C./min to 230° C. for 5 min. The mass spectrometer was operated in SIM mode. The MS source temperature was 230° C., the quadrupole temperature was 150° C., and the solvent delay was 3.55 min. Concentrations of target analytes were determined from calibration curves of each analyte. Calibration standards for 2-methyl-2-buten-2-ol, 3-methyl-2-buten-1-ol, 3-methyl-2-butenal, and linalool were prepared in 10 mL of deionized water at concentrations of 1, 10, and 100 ppm. The headspace for each calibration standard was analyzed using the same GC/MS-SIM method. Isoprene was calibrated from certified gas standards at 14, 135, and 1375 ppm. Linear correlation coefficients for calibration curves were ≥0.99 for all impurity components. FIG. 13 shows a gas chromatogram of authentic linalool acquired under the GC/MS-SIM conditions. FIG. 14 shows a gas chromatogram of authentic 2-methyl-3-buten-2-ol acquired under the GC-MS-SIM conditions.

Figure 15:
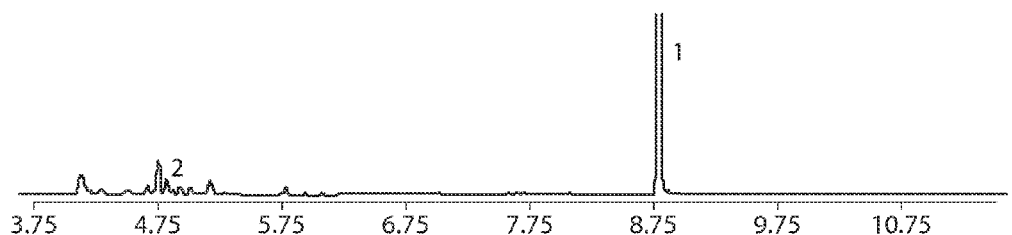
FIG. 15 shows a gas chromatogram of a 1 ml sample of headspace of a 20 ml vial containing *E. coli* BL21 harboring plasmid pJ401-NES1-idi cultured for 24 hours in Luria Bertani broth supplemented with 50 µg/ml kanamycin and 100 µM IPTG. Peak 1 is linalool, with a retention time of 8.8 minutes. Peak 2 is 2-methyl-3-buten-2-ol, with a retention time of 4.8 minutes. The peak at 4.75 minutes has been identified as 2-butanone.
Figure 16:
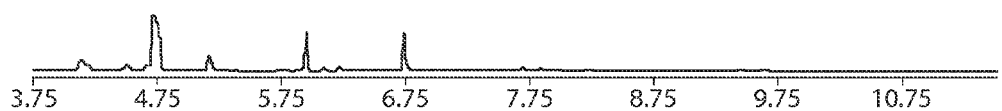
FIG. 16 shows a gas chromatogram of a 1 ml sample of headspace of a 20 ml vial containing *E. coli* BL21 harboring plasmid pJ404-SAAT cultured for 24 hours in Luria Bertani broth supplemented with 100 µg/ml ampicillin and 100 µM IPTG. Peaks corresponding to linalool and 2-methyl-3-buten-2-ol are absent. The peak at 4.75 minutes has been identified as 2-butanone.
Figure 17:
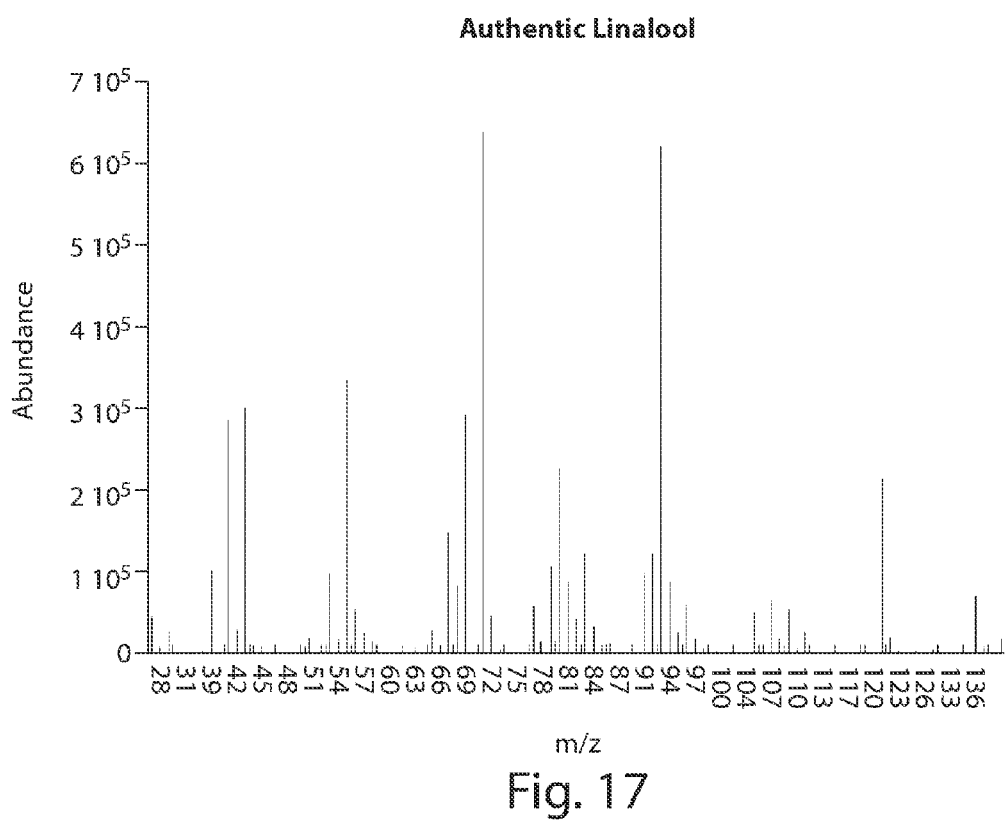
FIG. 17 shows the results of GC/MS analysis of authentic linalool.
Figure 18:
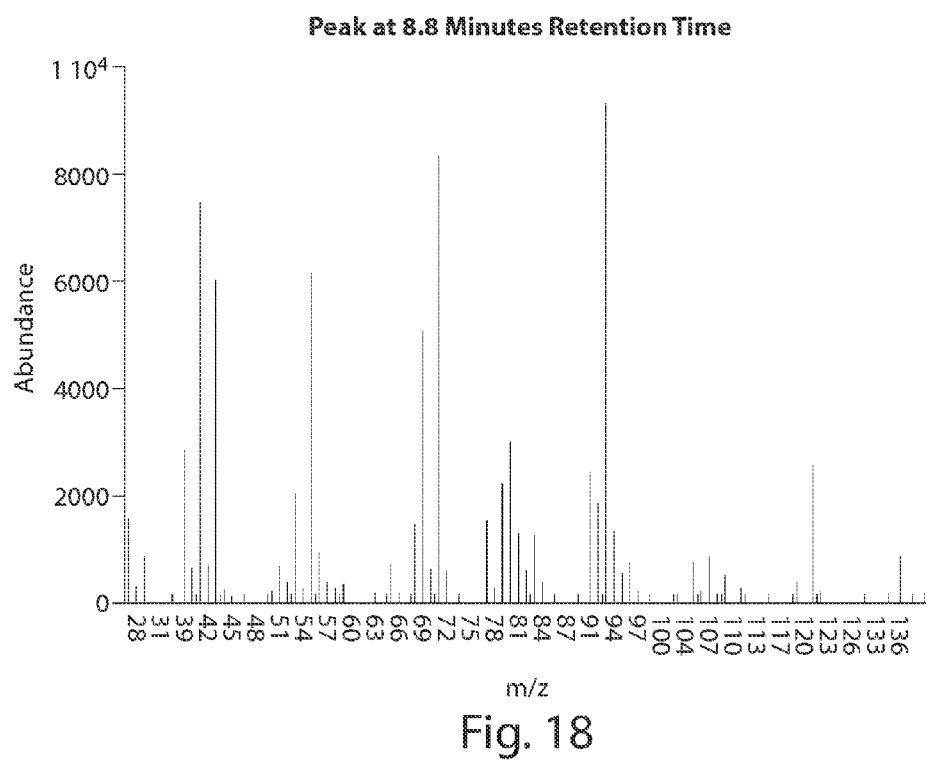
FIG. 18 shows the results of GC/MS analysis of the peak at 8.8 minutes from FIG. 15, verifying the identity of the peak as linalool.
Figure 19:
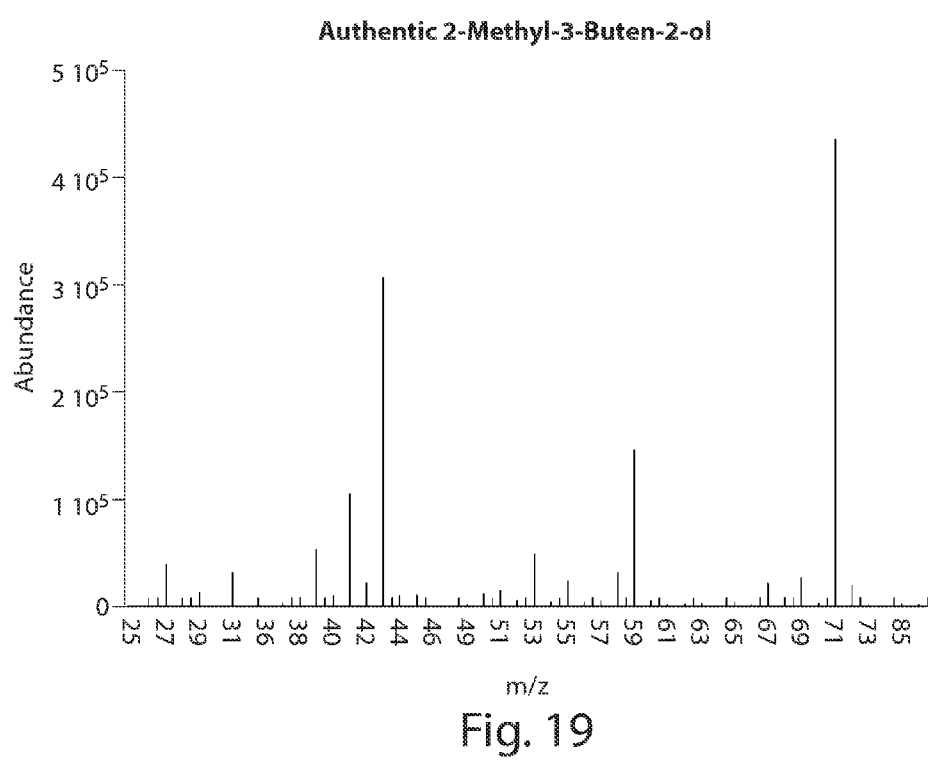
FIG. 19 shows the results of GC/MS analysis of authentic 2-methyl-3-buten-2-ol.
Figure 20:
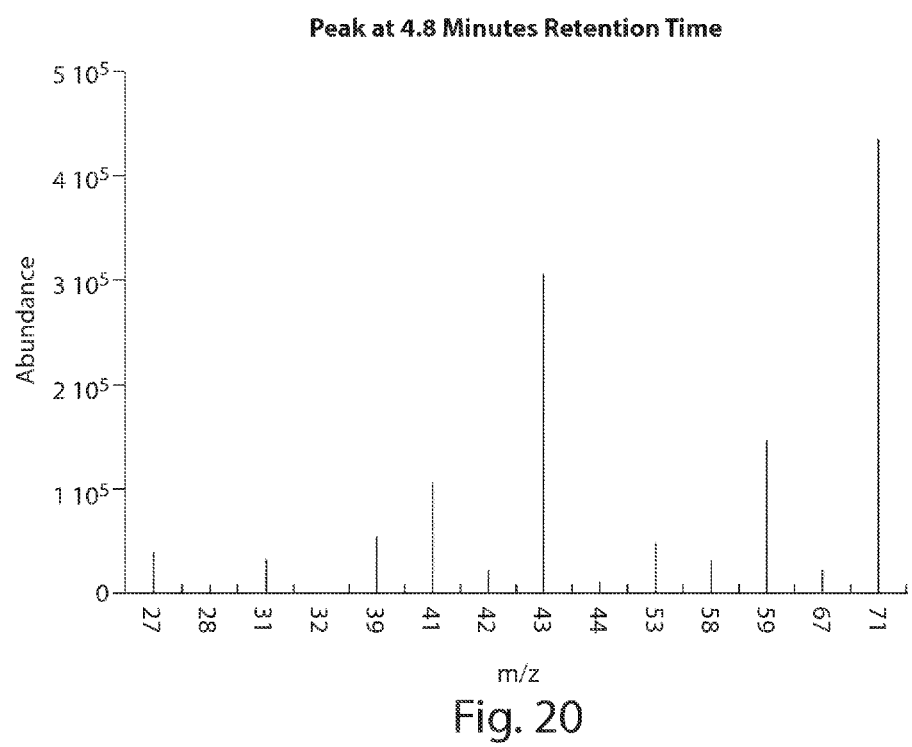
FIG. 20 shows the results of GC/MS analysis of the peak at 4.9 minutes from FIG. 15, verifying the identity of the peak as 2-methyl-3-buten-2-ol.

The results of this example are presented in FIG. 15. BL21 cells harboring pJ401-NES1-idi produced 1.47 mg/L linalool, corresponding to the peak at 8.8 minutes, and 0.05 mg/L 2-methyl-3-buten-2-ol, corresponding to the peak at 4.8 minutes. This demonstrates that *E. coli* cells harboring pJ401-NES1-idi produce 2-methyl-3-buten-2-ol in addition to linalool. The peaks corresponding to linalool and 2-methyl-3-buten-2-ol are absent from control cultures of BL21 harboring pJ404-SAAT grown under similar conditions (FIG. 16). The peaks were identified by the NIST 11 MS Library. The peaks for linalool (FIG. 17 and FIG. 18) and 2-methyl-3-buten-2-ol (FIG. 19 and FIG. 20) were also identified by comparison of retention times and ion fragmentation patterns against authentic samples.

EXAMPLE 4

Overexpression of Mevalonate Pathway to Improve 2-Methyl-3-Buten-2-Ol Production by FaNES1

This working example shows the production of 2-methyl-3-buten-2-ol from dimethylallyl diphosphate by a non-naturally occurring microorganism expressing an exogenous terpene synthase, the (3S,6E)-nerolidol synthase of *Fragaria ananassa*, can be enhanced by overexpression of a heterologous mevalonate pathway to increase the pool of dimethylallyl diphosphate available for conversion to 2-methyl-3-buten-2-ol.

The heterologous mevalonate pathway was constructed on a plasmid, pGB1036, as follows.

Plasmid pGA31R-MCS was constructed entirely by DNA synthesis, with the nucleotide sequence (SEQ ID NO: 5) presented in FIG. 21.

Plasmid pGS31R-MCS was constructed by replacing the p15A origin of replication on pGA31R-MCS with the low-copy pSC101 origin as an AvrII/SacI fragment using standard cloning techniques. The nucleotide sequence (SEQ ID NO: 6) is provided in FIG. 22.

Plasmid pJ248-mvaES was constructed using the codon-optimized sequence (SEQ ID NO: 7) of the mvaE and mvaS genes of *Enterococcus faecalis* ATCC 700802 (the codon-optimized sequences of mvaE and mvaS are as presented in FIG. 23). The mvaE and mvaS genes of *Enterococcus faecalis* ATCC 700802 were codon-optimized for expression in *E. coli*, synthesized and inserted in the plasmid pJ248. Unique ribosomal binding sites were included in front of each gene, along with flanking endonuclease restriction sites for use in plasmid construction.

Plasmid pJ241-MK.PMK.MPD.IDI containing a codon-optimized synthetic operon was constructed entirely by DNA synthesis, with the nucleotide sequence (SEQ ID NO: 8) presented in FIG. 24. The sequence of the synthetic operon, codon-optimized for expression in *E. coli*, encodes the mevalonate kinase gene of *Methanocaldococcus jannaschi*, the phosphomevalonate kinase of *Enterococcus faecalis* ATCC 700802, the mevalonate diphosphate decarboxylase of *Saccharomyces cerevisiae* S288C, and the isopentenyl diphosphate isomerase gene of *E. coli* MG1655, including incorporated ribosomal binding sites and flanking restriction endonuclease sites used in subsequent cloning steps.

Plasmid pGB1008 was constructed by cloning the optimized mvaES genes from pJ248-mvaES into pGA31R-MCS as a KpnI/MluI DNA fragment using standard cloning techniques.

Figure 25:
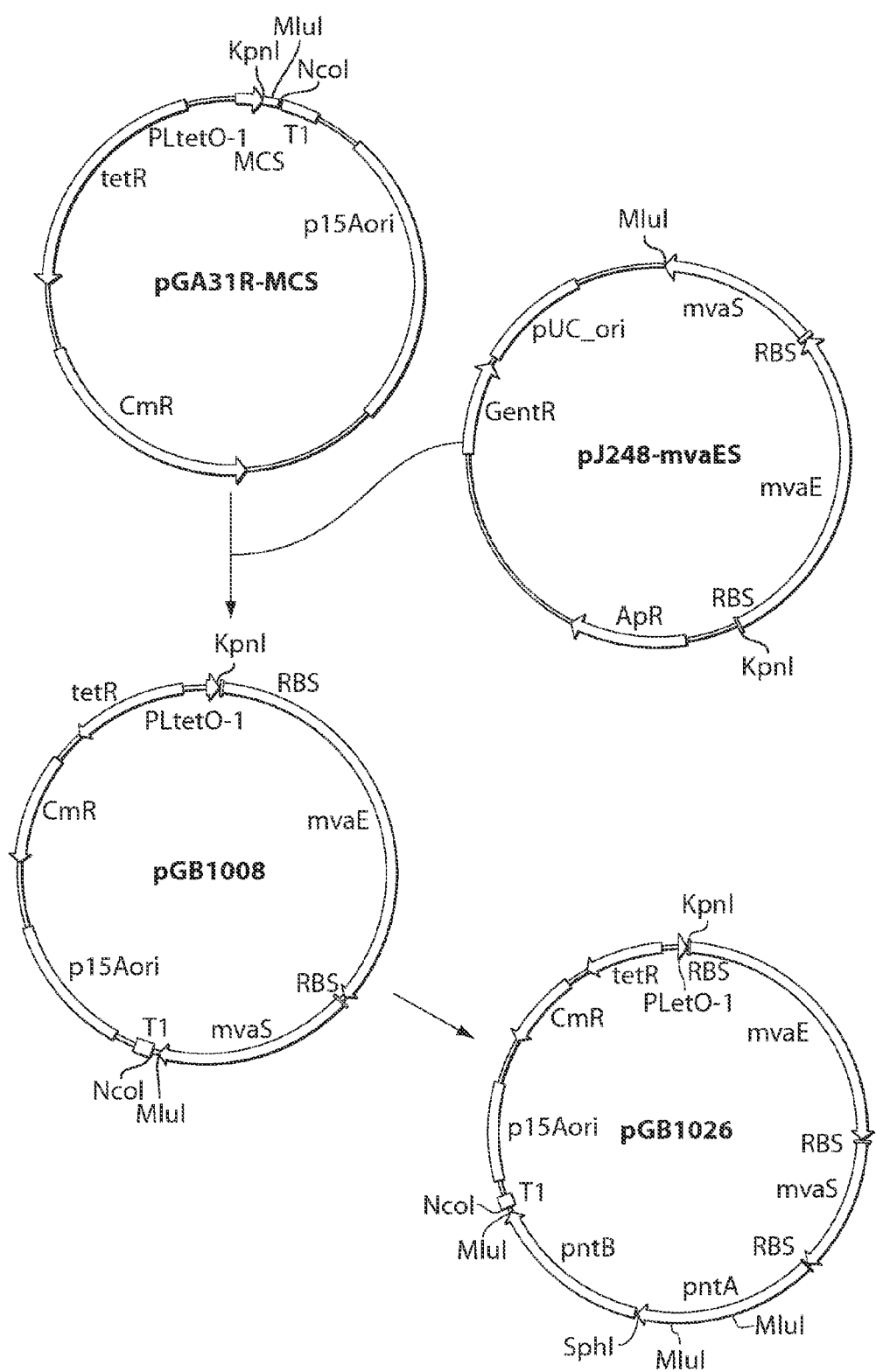
FIG. 25 shows a cloning strategy for the production of plasmid pGB1026.

Plasmid pGB1026. The cloning strategy for pGB1026 is presented in FIG. 25. Plasmid pGB1026 was constructed by inserting an approximately 3,000 base pair PCR product encoding the pntAB genes of *E. coli* into the MluI site of pGB1008. The PCR product encoding the pntAB genes was amplified from genomic DNA of MG1655 using AccuPrime Pfx polymerase with the following oligonucleotide primers:

Primer 1:
(SEQ ID NO: 9)
5'-CCG TAA CTA AAC GCG AAG GGA ATA TCA TGC GAA
TTG G-3'

Primer 2:
(SEQ ID NO: 10)
5'-CTA GAG ATC TAC GCG TCA GGG TTA CAG AGC TTT
C-3'

Primer 1 incorporates a ribosomal binding site in front of the start codon of pntA. Primers 1 and 2 also include appropriate vector-overlapping 5' sequences for use with the In-Fusion Advantage PCR Cloning Kit (Clontech). The PCR product was gel-purified, as was pGB1008 linearized with the restriction endonuclease MluI. Fragments were directionally joined together using the In-Fusion cloning kit and GC5 competent cells, following the manufacturer's directions. Transformants were screened, and the proper plasmid was identified through agarose gel electrophoresis of restriction endonuclease-digested plasmid DNAs.

Figure 26:
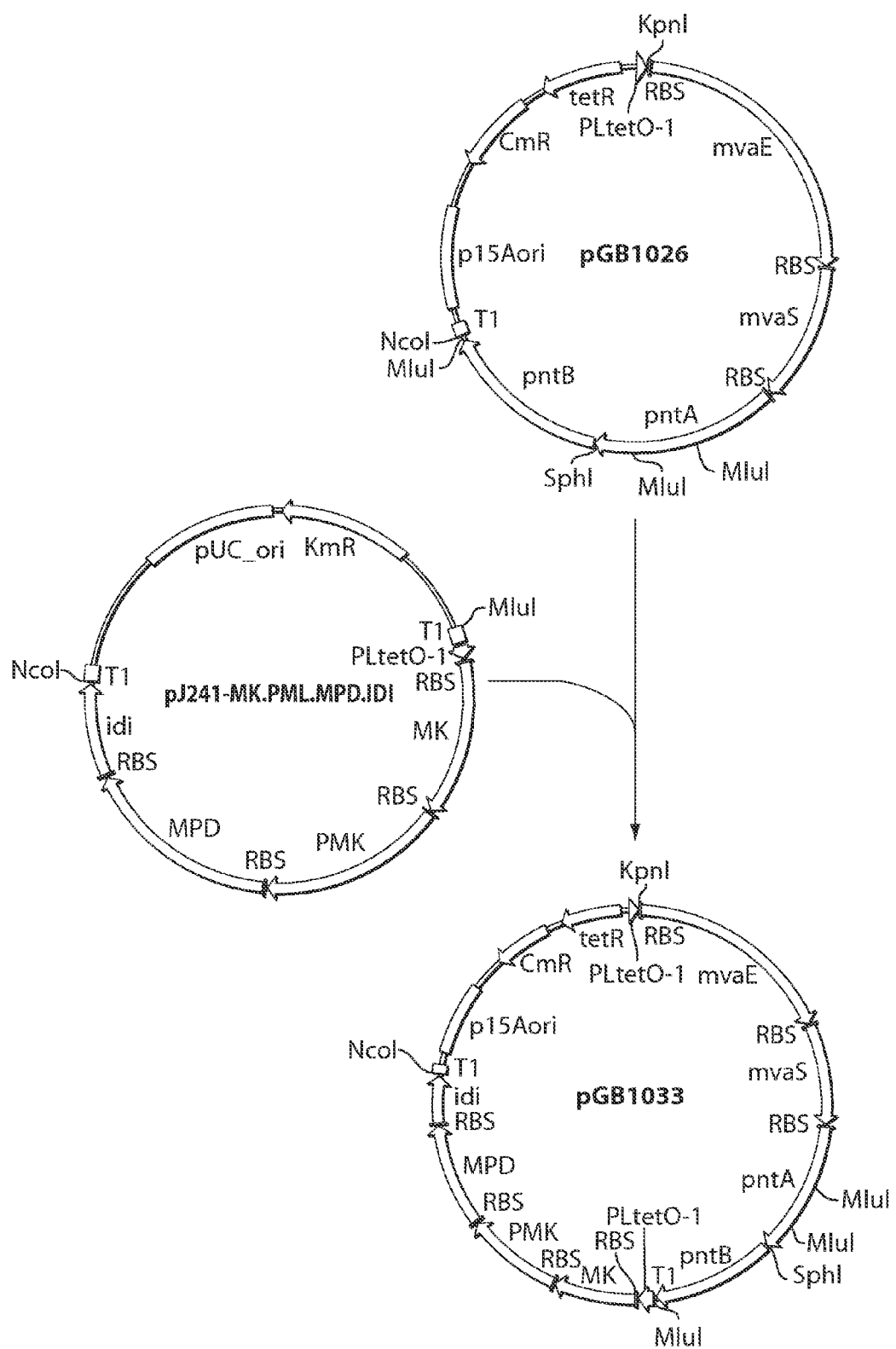
FIG. 26 shows a cloning strategy for the production of plasmid pGB1033.

Plasmid pGB1033 was created through the following process, illustrated in FIG. 26. pGB1026 was digested with the restriction endonucleases NcoI and SphI; the resulting 8.3 kb fragment was gel-purified. A second aliquot of pGB1026 was digested with the restriction endonucleases MluI and SphI; the resulting 1.4 kb fragment was gel-purified. Plasmid pJ241-MK.PMK.MPD.IDI was digested with the restriction endonucleases NcoI and MluI; the resulting 4.1 kb containing the synthetic operon was gel-purified. The fragments were ligated together in a trimolecular ligation reaction using the NEB Quick Ligation Kit (New England BioLabs) and transformed into GC5 competent cells. Transformants were screened, and the proper plasmid was identified through agarose gel electrophoresis of restriction endonuclease-digested plasmid DNAs.

Figure 27:
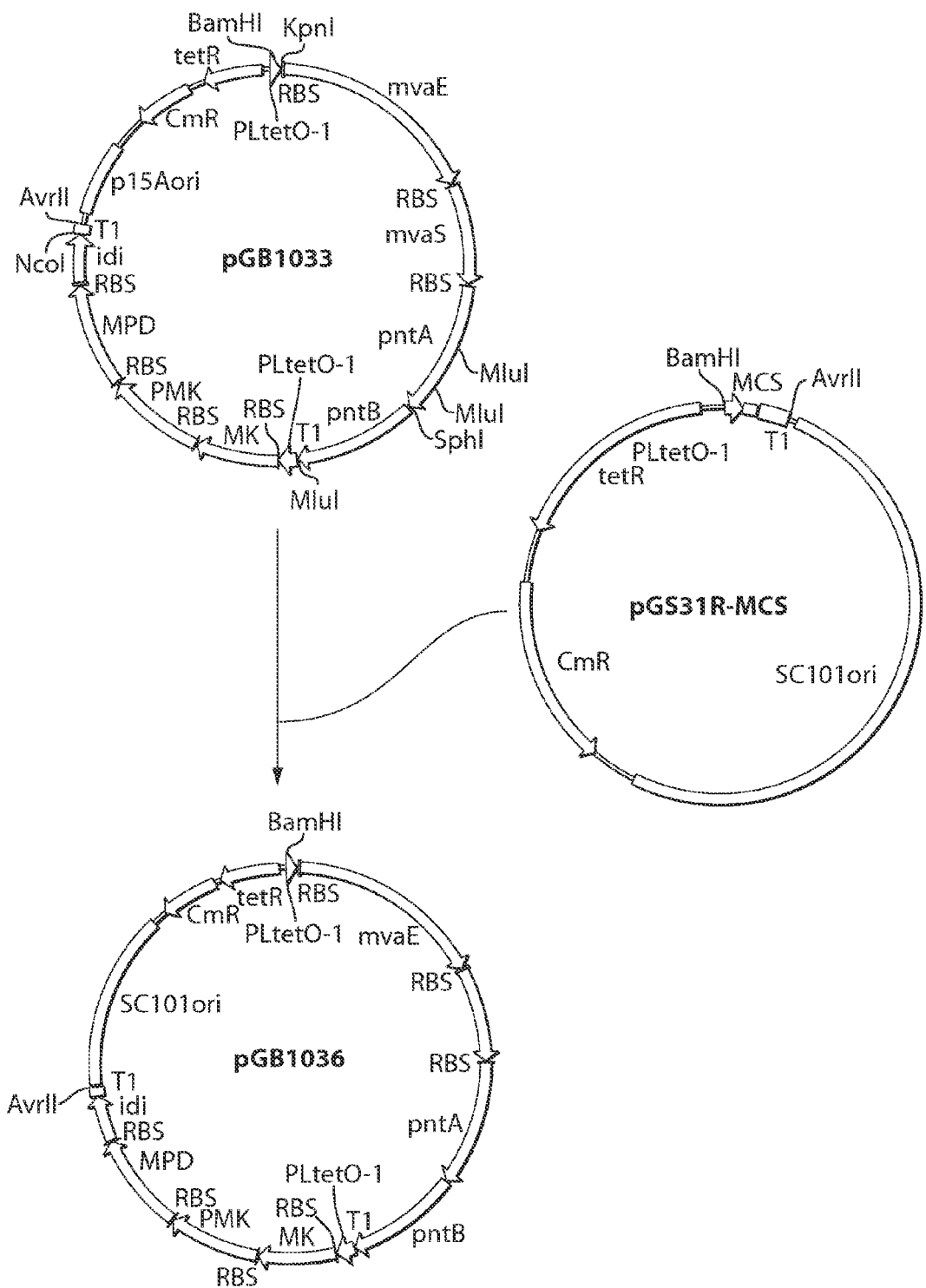
FIG. 27 shows a cloning strategy for the production of plasmid pGB1036.

Plasmid pGB1036 was constructed by cloning the 2 operons from pGB1033, complete with promoters and terminators into pGS31R-MCS as a BamHI/AvrII DNA fragment using standard cloning techniques, as illustrated in FIG. 27. The fragments were ligated together using the NEB Quick Ligation Kit (New England BioLabs) and transformed into GC5 competent cells. Transformants were screened, and the proper plasmid was identified through agarose gel electrophoresis of restriction endonuclease-digested plasmid DNAs.

Plasmids pGB1036 and pJ401-NES1-idi, were co-transformed by electroporation into E. coli BL21 electrocompetent cells.

The production of nerolidol, linalool and 2-methyl-3-buten-2-ol was assayed as follows. A single colony of BL21 harboring plasmids pJ401-NES1-idi and pGB1036 from an LB-agar plate was used to inoculate 10 ml of LB broth (10 g/L yeast extract, 5 g/L Bacto Tryptone, 10 g/L sodium chloride) containing 50 µg/ml kanamycin and 37 µg/ml chloramphenicol. Flasks were incubated for 16 hours at 37° C. in a rotary shaking incubator. After 16 hours, the cultures were diluted using fresh LB broth containing 50 µg/ml kanamycin, 20 µg/ml chloramphenicol, 200 µg/ml anhydrotetracycline, and 0.1 mM IPTG to yield an initial cell density at 600 nm of 0.4 to 0.5. 4 ml of the diluted culture was placed in a 20 ml GC vial and incubated for 6 or 24 hours at 30° C. with shaking. At 6 or 24 hours, the headspace gas was analyzed by GC/MS-SIM as described in Example 3.

Figure 28:
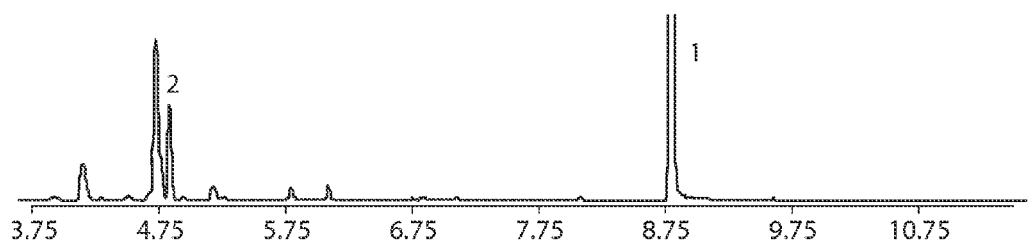
FIG. 28 shows a gas chromatogram of a 1 ml sample of headspace of a 20 ml vial containing *E. coli* BL21 harboring plasmids pJ401-NES1-idi and pGB1036 cultured for 24 hours in Luria Bertani broth supplemented with 50 µg/ml kanamycin, 20 µg/ml chloramphenicol, and 200 µg/ml anhydrotetracycline. Peak 1 is linalool, with a retention time of 8.8 minutes. Peak 2 is 2-methyl-3-buten-2-ol, with a retention time of 4.8 minutes. The peak at 4.75 minutes has been identified as 2-butanone.

The results of this example are presented in FIG. 28. BL21 cells harboring pJ401-NES1-idi and pGB1036 produced approximately 4.05 mg/L linalool, corresponding to the peak at 8.8 minutes, and 0.38 mg/L 2-methyl-3-buten-2-ol, corresponding to the peak at 4.8 minutes. This demonstrates that E. coli cells harboring pJ401-NES1-idi and pGB1036 produce over 7 times more 2-methyl-3-buten-2-ol than cells harboring pJ401-NES1-idi by itself.

EXAMPLE 5

FaNES1 Mutations that Alter the Linalool to 2-Methyl-3-Buten-2-Ol Ratio

This working example shows that the introduction of mutations into FaNES1 can alter the amount of linalool produced as compared to the amount of 2-methyl-3-buten-2-ol produced.

Site-directed mutagenesis or complete gene synthesis were used to introduce specific amino acid substitutions into the wild-type FaNES1 amino acid sequence. Table 4 presents the names of the mutant enzymes and the associated mutations. The amino acid numbering presented in Table 4 and this example correspond with the amino acid positions in the wild-type FaNES1 enzyme as reported in GenBank accession no. P0CV94.

TABLE 4

| Enzyme Name | Introduced Mutation(s) |
|---|---|
| NES1v2 | I266F, S374F and I490F |
| NES1#1 | I266F |
| NES1#2 | S374F |
| NES1#3 | I490F |
| NES1#4 | G375D |
| NES1#5 | I266F and S374F |
| NES1#6 | I266F and I490F |
| NES1#7 | S374F and I490F |
| NES1#8 | L413F |
| NES1#9 | I490K |
| NES1#10 | I490Y. |

NESv2 was produced from plasmid pJ401-NES1v2-idi using the codon-optimized sequence of the FaNES1 and the H. pluvialis idi genes. During construction, three amino acid mutations were introduced, converting the isoleucine at position 266 to phenylalanine (I266F), the serine at position 374 to phenylalanine (S374F), and the isoleucine at position 490 to phenylalanine (I490F).

FaNES1 mutants NES1#1 through NES1#10 were created through standard site-directed mutagenesis techniques using plasmid pJ401-NES1v2-idi as a template. The site-directed mutations were confirmed through DNA sequencing. Confirmed mutants were electroporated into E. coli BL21 electrocompetent cells. The production of linalool and 2-methyl-3-buten-2-ol for each individual mutant was assayed according to the methods described in Example 3, with a culture time of 6 hours at 30° C. The results are presented in Table 5.

TABLE 5

| FaNES1 Variant Enzyme | Linalool (mg/L) | 2-methyl-3-buten-2-ol (mg/L) |
|---|---|---|
| Wild-type | 0.54 | 0.02 |
| NESv2 | — | — |
| NES#1 | — | — |
| NES#2 | — | — |
| NES#3 | — | — |
| NES#4 | — | — |
| NES#5 | — | — |
| NES#6 | — | — |
| NES#7 | — | — |
| NES#8 | 0.05 | — |
| NES#9 | — | — |
| NES#10 | — | —. |

Since it had been shown (Example 4) that increasing the supply of dimethylallyl diphosphate results in increased production of linalool and 2-methyl-3-buten-2-ol by wild-type FaNES1, a subset of the plasmids encoding FaNES1 variants were co-transformed with pGB1036 into BL21 electrocompetent cells. The ability of the variant enzymes to produce linalool and 2-methyl-3-buten-2-ol was assayed according to the methods presented in Example 3, with a 24 hour incubation at 30° C. The results are presented in Table 6.

TABLE 6

| FaNES1 Variant Enzyme* | Lin* (mg/L) | 232-MB* (mg/L) |
|---|---|---|
| Wild-type | 4.05 | 0.38 |
| NES1#1 |  | 0.04 |
| NES1#3 | 0.08 | 0.04 |
| NES1#8 | 0.79 | 0.05 |
| NES1#9 | XX | XX |
| NES1#10 | XX | XX. |

*In vivo assay performed with enhanced dimethylallyl diphosphate concentrations provided by pGB1036; Lin = Linalool; 232-MB = 2-methyl-3-buten-2-ol.

EXAMPLE 6

Microorganism for the Production of Isoprene from Dimethylallyl Diphosphate

This example demonstrates how one may produce isoprene with a non-naturally occurring microorganism expressing a phosphatase, a 2-methyl-3-buten-2-ol isomerase, and a 2-methyl-3-buten-2-ol dehydratase.

The yhfR gene of Bacillus subtilis was codon-optimized for expression in E. coli, synthesized and inserted into the plasmid vector pJex404 to produce pJex404-yhfR. The codon-optimized yhfR sequence (SEQ ID NO: 3), including a ribosome binding site, is presented in FIG. 11. The ribosome binding site and yhfR coding sequence were amplified by polymerase chain reaction (PCR) using the following oligonucleotide primers:

(SEQ ID NO: 11)
5'-GGG CAA GTA ACT CGA TTA AAG AGG AGA AAA TAT AAT GAC GGC AG-3'

(SEQ ID NO: 12)
5'-GCC CTT GGG GCT CGA GTT ATT TGA TGA AAC CGC TCA GAT GG-3'

Plasmid pJ404-LDI was linearized by endonuclease restriction with the enzyme XhoI. The PCR product containing the yhfR coding sequence and the XhoI-digested pJ404-LDI were agarose gel-purified using standard laboratory techniques. The fragments were joined together using the In-Fusion Advantage PCR Cloning Kit (Clontech Laboratories, Inc., Mountain View, Calif.), then transformed into chemically competent E. coli GC5 cells (Gene Choice, available from Sigma-Aldrich Co. LLC) following the manufacturer's directions. Transformants were screened, and the proper plasmid was identified through agarose gel electrophoresis of restriction endonuclease-digested plasmid DNAs. The proper plasmid was then transformed into electrocompetent E. coli BL21. The resulting plasmid was designated pJ404-LDI.yhfR.

The production of isoprene by BL21 harboring plasmid pJ404-LDI.yhfR may be assayed as follows. A single colony of BL21 harboring pJ404-LDI.yhfR or pJ404-LDI from LB-agar plates are used to inoculate 10 mL of LB broth (10 g/L yeast extract, 5 g/L Bacto Tryptone, 10 g/L sodium chloride) containing 20 g/L glycerol and 100 µg/ml ampicillin contained in 125 mL Erlenmeyer flasks. Flasks are incubated for 16 hours at 37° C. in a rotary shaking incubator. After 16 hours, the cultures are diluted using fresh LB broth containing 20 g/L glycerol and 100 µg/ml ampicillin to an optical density of 0.16 at 600 nm. 50 ml of the diluted cultures are placed in 300-mL Erlenmeyer flasks and incubated at 37° C. in a rotary shaking incubator until the optical density at 600 nm reaches approximately 0.6, typically 90 minutes. 4 ml of the cultures are then placed into 20 ml gas chromatography headspace vials. IPTG (Isopropyl β-D-1-thiogalactopyranoside) is added to 0.1 mM. Cultures are grown for 16 hours at 37° C. with shaking.

Isoprene, 3-methyl-2-buten-1-ol and 2-methyl-3-buten-2-ol are measured as above. The identity of the isoprene peak may be verified using GC/MS, as described above.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While the foregoing is directed to embodiments of the present invention, other and further embodiments of the invention may be devised without departing from the basic scope thereof, and the scope thereof is determined by the claims that follow.

What is claimed is:

1. A non-naturally occurring microbial organism comprising an isoprene biosynthetic pathway for the conversion of dimethylallyl diphosphate (DMAPP) to isoprene, wherein the isoprene biosynthetic pathway comprises the conversion of DMAPP to 2-methyl-3-buten-2-ol followed by the conversion of 2-methyl-3-buten-2-ol to isoprene and wherein the isoprene biosynthetic pathway comprises an exogenous nucleic acid encoding at least one 2-methyl-3-buten-2-ol synthase capable of converting DMAPP to 2-methyl-3-buten-2-ol and an exogenous nucleic acid encoding at least one 2-methyl-3-buten-2-ol dehydratase capable of converting 2-methyl-3-buten-2-ol to isoprene and wherein the isoprene biosynthetic pathway is expressed at a sufficient level to produce isoprene.

2. The non-naturally occurring microbial organism of claim 1, wherein the organism overexpresses one or more endogenous or exogenous genes encoding at least one enzyme selected from: an enzyme of the methylerythritol phosphate pathway or an enzyme of the mevalonate pathway.

3. The non-naturally occurring microbial organism of claim 2, wherein the dimethylallyl diphosphate available for conversion to isoprene is increased.

4. The non-naturally occurring microbial organism of claim 1, wherein the 2-methyl-3-buten-2-ol dehydratase is a linalool dehydratase-isomerase.

5. The non-naturally occurring microbial organism of claim 4, wherein the 2-methyl-3-buten-2-ol dehydratase is a linalool dehydratase-isomerase derived from *Castellaniella defragrans*.

6. The non-naturally occurring microbial organism of claim 1, further comprising one or more endogenous or exogenous genes encoding at least one enzyme of the methylerythritol phosphate pathway selected from: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, 1-hydroxy-2-methyl-2-(E)-butenyl-4-diphosphate synthase, dimethylallyl-diphosphate/isopentenyl-diphosphate:NAD(P)$^+$ oxidoreductase, isopentenyl diphosphate isomerase, and combinations thereof.

7. The non-naturally occurring microbial organism of claim 1, further comprising one or more endogenous or exogenous genes encoding at least one enzyme of the mevalonate pathway selected from: acetyl-CoA acetyltransferase, 3-hydroxy-3-methylglutaryl-CoA synthase, 3-hydroxy-3-methylglutaryl-CoA reductase, mevalonate kinase, phosphomevalonate kinase, diphosphomevalonate decarboxylase, isopentenyl-diphosphate isomerase and combinations thereof.

8. The non-naturally occurring microbial organism of claim 1, wherein the microbial organism is selected from bacteria, archaea, eubacteria, yeast and fungi.

9. The non-naturally occurring microbial organism of claim 1, wherein the microbial organism is an *Escherichia coli*.

10. The non-naturally occurring microbial organism of claim 1, wherein the 2-methyl-3-buten-2-ol synthase is a terpene synthase.

11. The non-naturally occurring microbial organism of claim 10, wherein the terpene synthase is a linalool synthase.

12. The non-naturally occurring microbial organism of claim 11, wherein the linalool synthase is derived from *Clarkia breweri, Arabidopsis thaliana, Perilla setoyensis, Perilla frutescans, Actinidia arguta, Actinidia polygama, Artemesia annua, Ocimum basilicum,* or *Mentha aquatica*.

13. The non-naturally occurring microbial organism of claim 10, wherein the terpene synthase is a nerolidol synthase.

14. The non-naturally occurring microbial organism of claim 13, wherein the nerolidol synthase is derived from *Fragaria ananassa*.

15. The non-naturally occurring microbial organism of claim 2, wherein the at least one enzyme of the methylerythritol phosphate pathway is selected from: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2-C-methyl-D-erythritol-2,4-cyclodiphosphate synthase, 1-hydroxy-2-methyl-2-(E)-butenyl-4-diphosphate synthase, dimethylallyl-diphosphate/isopentenyl-diphosphate:NAD(P)$^+$ oxidoreductase, isopentenyl diphosphate isomerase, and combinations thereof.

16. The non-naturally occurring microbial organism of claim 15, wherein the at least one enzyme of the methylerythritol phosphate pathway is selected from: 1-deoxy-D-xylulose-5-phosphate synthase, 1-deoxy-D-xylulose-5-phosphate reductoisomerase and isopentenyl diphosphate isomerase.

17. The non-naturally occurring microbial organism of claim 2, wherein the at least one enzyme of the mevalonate pathway is selected from: acetyl-CoA acetyltransferase, 3-hydroxy-3-methylglutaryl-CoA synthase, 3-hydroxy-3-methylglutaryl-CoA reductase, mevalonate kinase, phospho-mevalonate kinase, diphosphomevalonate decarboxylase, isopentenyl-diphosphate isomerase and combinations thereof.

18. A non-naturally occurring microbial organism of claim 1, wherein the dimethylallyl diphosphate available for conversion to isoprene is increased.

19. A method of producing isoprene, the method comprising the steps of culturing a non-naturally occurring microbial organism of claim 1 in a suitable culture medium containing a carbon source under conditions such that the non-naturally occurring microorganism converts at least a part of the carbon source to isoprene, and optionally recovering the isoprene.

20. The method of claim 19, wherein at least one enzyme of a methylerythritol phosphate pathway or the mevalonate pathway is overexpressed by the organism.

* * * * *